US008053198B2

(12) United States Patent
Mathew et al.

(10) Patent No.: US 8,053,198 B2
(45) Date of Patent: Nov. 8, 2011

(54) DIAGNOSTIC METHODS

(75) Inventors: Anu Mathew, North Potomac, MD (US); Martin Stengelin, Gaithersburg, MD (US); Eli Glezer, Chevy Chase, MD (US)

(73) Assignee: Meso Scale Technologies, LLC, Gaithersburg, MD (US)

( * ) Notice: Subject to any disclaimer, the term of this patent is extended or adjusted under 35 U.S.C. 154(b) by 0 days.

(21) Appl. No.: 12/209,701

(22) Filed: Sep. 12, 2008

(65) Prior Publication Data

US 2009/0075299 A1    Mar. 19, 2009

Related U.S. Application Data

(60) Provisional application No. 60/993,864, filed on Sep. 14, 2007.

(51) Int. Cl.
*G01N 33/53*    (2006.01)
(52) U.S. Cl. ......................................... 435/7.1
(58) Field of Classification Search .................. None
See application file for complete search history.

(56) References Cited

U.S. PATENT DOCUMENTS

| | | | |
|---|---|---|---|
| 4,168,146 A | 9/1979 | Grubb et al. | |
| 4,235,601 A | 11/1980 | Deutsch et al. | |
| 4,366,241 A | 12/1982 | Tom et al. | |
| 4,442,204 A | 4/1984 | Greenquist et al. | |
| 5,208,535 A | 5/1993 | Nakayama et al. | |
| 5,807,522 A | 9/1998 | Brown et al. | |
| 6,110,426 A | 8/2000 | Shalon et al. | |
| 2003/0113713 A1 | 6/2003 | Glezer et al. | |
| 2003/0207290 A1 | 11/2003 | Kenten et al. | |
| 2004/0022677 A1 | 2/2004 | Wohlstadter et al. | |
| 2004/0189311 A1 | 9/2004 | Glezer et al. | |
| 2005/0052646 A1 | 3/2005 | Wohlstadter et al. | |
| 2005/0142033 A1 | 6/2005 | Glezer et al. | |
| 2006/0205012 A1 | 9/2006 | Debad et al. | |

FOREIGN PATENT DOCUMENTS

WO    WO 99/26067    5/1999
WO    WO 2004/058055 A2    7/2004

OTHER PUBLICATIONS

Tockman et al (Cancer Res., 1992, 52:2711s-2718s).*
Swidzinska et al (Pneumonol Alegol Pol, 2004, 72(9-10): abstract).*
Tas et al (Melanoma Research, 2006, 16(5): abstract.*
Alberts et al. (Molecular Biology of the Cell, 3rd edition, 1994, p. 465).*
Greenbaum et al. (Genome Biology, 2003, vol. 4, Issue 9, pp. 117.1-117.8).*
Yokoyama et al (Gynecologic Oncology, 2000, 77:413-418).*
Kumar et al (Anticancer Research, 2002, 22(3): 1877-1880).*
Yokoe et al (Breast Cancer, 2000, 7(3): abstract).*
Benoy et al (Clin Breast Cancer, 2002, 2(4):abstract).*
Benoy et al (Clin Breast Cancer, 2002, 2(4):311-315).*
Climente et al (Clin Transl Oncol., Jun. 2006, 8(6): Abstract).*
Chen et al (Gynecologic Oncology, 2004, 630-635).*
Zhao et al (Cancer Research, 2009, 69(19): 7696-7703).*
Aref S. et al., "Soluble VEGF/sFLt1 Ratio is an Independent Predictor of AML Patient Out Come", *Hematology* 10 (2):131-134 (2005).
Aung PP et al., "Systematic Search for Gastric Cancer-Specific Genes Based on SAGE Data: Melanoma Inhibitory Activity and Matrix Metalloproteinase-10 are Novel Prognostic Factors in Patients with Gastric Cancer", *Oncogen* 25:2546-2557 (2006).
Bando H. et al., "Association Between Intratumoral Free and Total VEGF, Soluble VEGFR-1, VEGFR-2 and Prognosis in Breast Cancer", *British Journal of Cancer* 92:553-561 (2005).
Baron A.T. et al., "Soluble Epidermal Growth Factor Receptor (SEG-FR) and Cancer Antigen 125 (CA125) as Screening and Diagnostic Tests for Epithelial Ovarian Cancer", *Cancer Epidemiology Biomarkers Prevention* 14(2):306-318 (2005).
Buller R.E. et al., "CA 125 Kinetics: A Cost-Effective Clinical Tool to Evaluate Clinical Trial Outcomes in the 1990s", *American Journal of Obstetrics and Gynecology* 174:1241-1254 (1996).
Buys S.S. et al., "Ovarian Cancer Screening in the Prostate, Lung, Colorectal and Ovarian (PLCO) Cancer Screening Trial: Findings from the Initial Screen of Randomized Trial", *American Journal of Obstetrics and Gynecology* 193:1630-1639 (2005).
Caine G.J. et al., "Changes in Plasma Vascular Endothelial Growth Factor, Angiopoietins, and Their Receptors Following Surgery for Breast Cancer", *Cancer Letters* 248:131-136 (2007).
Chen H. et al., "VEGF, VEGFRs Expressions and Activated STATs in Ovarian Epithelial Carcinoma", *Gynecologic Oncology* 94(3):630-635 (2004).
Cooper B.C. et al., "Preoperative CA 125 Levels: An Independent Prognostic Factor for Epithelial Ovarian Cancer", *Obstetrics & Gynecology* 100(1):59-64 (2002).
Dales JP et al., "Prediction of Metastasis Risk (11 Year Follow-Up) Using VEGF-RI, VEGF-R2, Tie-2/Tek and CD105 Expression in Breast Cancer (n=905)", *British Journal of Cancer* 90(6):1216-1221 (2004).
Debad J.D. et al., "Clinical and Biological Applications of ECL", *Electrogenerated Chemiluminescence* pp. 359-396 (2004).
Enjoji M. et al., "Clinical Significance of Serum Levels of Vascular Endothelial Growth Factor and its Receptor in Biliary Disease and Carcinoma", *World Journal of Gastroenterology* 11(8):1167-1171 (2005).
Gill J.H. et al., "MMP-10 is Overexpressed, Proteolytically Active, and a Potential Target for Therapeutic Intervention in Human Lung Carcinomas", *Neoplasia* 6(6):777-785 (2004).
Gorelik E. et al., "Multiplexed Immunobead-Based Cytokine Profiling for Early Detection of Ovarian Cancer", *Cancer Epidemiology, Biomarkers & Prevention* 14(4):981-987 (2005).

(Continued)

*Primary Examiner* — Sean Aeder
(74) *Attorney, Agent, or Firm* — Scully, Scott, Murphy & Presser, P.C.

(57) ABSTRACT

The present invention relates to methods of diagnosing cancerous conditions in a patient, as well as methods of monitoring the progression of a cancerous condition and/or methods of monitoring a treatment protocol of a therapeutic agent or a chemotherapeutic regimen. The invention also relates to assay methods used in connection with the diagnostic methods described herein.

26 Claims, 24 Drawing Sheets

OTHER PUBLICATIONS

Guidi A.J. et al., "Expression of Vascular Permeability Factor (Vascular Endothelial Growth Factor) and its Receptors in Endometrial Carcinoma", *Cancer* 78(3):454-460 (1996).

Hoar F.J. et al., "Circulating Levels of VEGF-A, VEGF-D and Soluble VEGF-A Receptor (sFlt-1) in Human Breast Cancer", *The International Journal of Biological Markers* 19(3):229-235 (2004).

Hellstrom I. et al., "Mesothelin Variant 1 is Released from Tumor Cells as a Diagnostic Marker", *Cancer Epidemiology, Biomarkers & Prevention* 15(5):1014-1020 (2006).

Hsieh F-C et al., "Evaluation of Potential Stat3-Regulated Genes in Human Breast Cancer", *Biochemical and Biophysical Research Communications* 335(2):292-299 (2005).

Iihan N. et al., "Functional Significance of Vascular Endothelial Growth Factor and its Receptor (Receptor-1) in Various Lung Cancer Types", *Clinical Biochemistry* 37(9):840-845 (2004).

Inan S. et al., "Immunolocalizations of VEGF, its Receptors Flt-1, KDR and TGF-β's in Epithelial Ovarian Tumors", *Histol Histopathol* 21(10):1055-1064 (2006).

Jacobs I.J. et al., "Progress and Challenges in Screening for Early Detection of Ovarian Cancer", *Molecular & Cellular Proteomics* 3(4):355-366 (2004).

Kodama J. et al., "Serum C-Reactive Protein as a Prognostic Factor in Patients with Epithelial Ovarian Cancer", *European Journal of Obstetrics & Gynecology and Reproductive Biology* 82(1):107-110 (1999).

Kumar H. et al., "Soluble FLT-1 is Detectable in the Sera of Colorectal and Breast Cancer Patients", *Anticancer Research* 22(3):1877-1880 (2002).

Le Page C. et al., "From Gene Profiling to Diagnostic Markers: IL-18 and FGF-2 Complement CA125 as Serum-Based Markers in Epithelial Ovarian Cancer", *Int. J. Cancer* 118(7):1750-1758 (2006).

Lokshin A.E. et al., "Circulating IL-8 and Anti-IL-8 Autoantibody in Patients with Ovarian Cancer", *Gynecologic Oncology* 102(2):244-251 (2006).

Macciò A. et al., "High Serum Levels of Soluble IL-2 Receptor, Cytokines, and C Reactive Protein Correlate with Impairment of T Cell Response in Patients with Advanced Epithelial Ovarian Cancer", *Gynecologic Oncology* 69(3):248-252 (1998).

Mathew R. et al., "Stromelysin-2 Overexpression in Human Esophageal Squamous Cell Carcinoma: Potential Clinical Implications", *Cancer Detection and Prevention* 26(3):222-228 (2002).

Matsumoto K. et al., "Prognostic Significance of Plasma Placental Growth Factor Levels in Renal Cell Cancer: An Association with Clinical Characteristics and Vascular Endothelial Growth Factor Levels", *Anticancer Research* 23(6D):4953-4958 (2003).

McCluggage W.G. et al., "Immunohistochemistry as a Diagnostic Aid in the Evaluation of Ovarian Tumors", *Seminars in Diagnostic Pathology* 22(1):3-32 (2005).

Meunier-Carpentier S. et al., "Comparison of the Prognosis Indication of VEGFR-1 and VEGFR-2 and Tie2 Receptor Expression in Breast Carcinoma", *International Journal of Oncology* 26(4):977-984 (2005).

Miyata Y. et al., "Expression of Matrix Metalloproteinase-10 in Renal Cell Carcinoma and its Prognostic Role", *European Urology* 52(3):791-797 (2007).

Mor G. et al., "Serum Protein Markers for Early Detection of Ovarian Cancer", *PNAS* 102(21):7677-7682 (2005).

Moradi M.M. et al,. "Serum and Ascitic Fluid Levels of Interleukin-1, Interleukin-6, and Tumor Necrosis Factor-Alpha in Patients with Ovarian Epithelial Cancer", *Cancer* 72(8):2433-2440 (1993).

Moshkovskii S.A. et al., "Ovarian Cancer Marker of 11.7 kDa Detected by Proteomics is a Serum Amyloid A1", *Proteomics* 5(14):3790-3797 (2005).

Olivier R.I. et al., "CA125 and Transvaginal Ultrasound Monitoring in High-Risk Women Cannot Prevent the Diagnosis of Advanced Ovarian Cancer", *Gynecologic Oncology* 100(1):20-26 (2006).

Orbe J. et al., "Independent Association of Matrix Metalloproteinase-10, Cardiovascular Risk Factors and Subclinical Atherosclerosis", *Journal of Thrombosis and Haemostasis* 5(1):91-97 (2007).

Parr C. et al., "Placenta Growth Factor is Over-Expressed and Has Prognostic Value in Human Breast Cancer", *European Journal of Cancer* 41(18):2819-2827 (2005).

Penson R.T. et al., "Cytokines IL-1β, IL-2, IL-6, IL-8, MCP-1, GM-CSF and TNFα in Patients with Epithelial Ovarian Cancer and Their Relationship to Treatment with Paclitaxel", *International Journal of Gynecological Cancer* 10(1):33-41 (2000).

Relf M. et al., "Expression of the Angiogenic Factors Vascular Endothelial Cell Growth Factor, Acidic and Basic Fibroblast Growth Factor, Tumor Growth Factor β-1, Platelet-Derived Endothelial Cell Growth Factor, Placenta Growth Factor, and Pleiotrophin in Human Primary Breast Cancer and its Relation to Angiogenesis", *Cancer Research* 57(5):963-969 (1997).

Rosen D.G. et al., "Potential Markers that Complement Expression of CA125 in Epithelial Ovarian Cancer", *Gynecologic Oncology* 99(2):267-277 (2005).

Scholler N. et al., "Bead-Based ELISA for Validation of Ovarian Cancer Early Detection Markers", *Clin Cancer Res* 12(7):2117-2124 (2006).

Seargent J.M. et al., "Expression of Matrix Metalloproteinase-10 in Human Bladder Transitional Cell Carcinoma", *Urology* 65(4):815-820 (2005).

Terry K.L. et al., "Blood and Urine Markers for Ovarian Cancer: A Comprehensive Review", *Disease Markers* 20(2):53-70 (2004).

Toi M. et al., "Significance of Vascular Endothelial Growth Factor (VEGF)/Soluble VEGF Receptor-1 Relationship in Breast Cancer", *Int. J. Cancer* 98(1):14-18 (2002).

Ülkü A.S. et al., "Essential Role of Raf in Ras Transformation and Deregulation of Matrix Metalloproteinase Expression in Ovarian Epithelial Cells", *Molecular Cancer Research* 1(14):1077-1088 (2003).

Van Haaften-Day C. et al., "OVX1, Macrophage-Colony Stimulating Factor, and CA-125-II as Tumor Markers for Epithelial Ovarian Carcinoma: A Critical Appraisal", *Cancer* 92(11):2837-2844 (2001).

Wei S-C et al., "Placenta Growth Factor Expression is Correlated with Survival of Patients with Colorectal Cancer", *Gut* 54(5):666-672 (2005).

Zhang X. et al., "Expression of MMP-10 in Lung Cancer", *Anticancer Research* 27(4C):2791-2795 (2007).

Zohrabian V.M. et al., "Gene Expression Profiling of Metastatic Brain Cancer", *Oncology Reports* 18(2):321-328 (2007).

Skates S.J. et al., "Pooling of Case Specimens to Create Standard Serum Sets for Screening Cancer Biomarkers", *Cancer Epidemiol Biomarkers Prev.* 16(2):334-341 (2007).

Delehanty J.B., "Printing Functional Protein Microarrays Using Piezoelectric Capillaries", Methods in Molecular Biology 264:135-143 (2004).

Lue R.Y.P. et al., "Site-Specific Immobilization of Biotinylated Proteins for Protein Microarray Analysis", *Methods in Molecular Biology* 264:85-100 (2004).

Lovett R.A., "Toxicogenomics: Toxicologists Brace for Genomics Revolution", *Science* 289(5479):536-537 (2000).

Berns A., "Gene Expression in Diagnosis", *Cancer* 403:491-492 (2000).

Walt D.R., "Molecular Biology: Bead-Based Fiber-Optic Arrays", *Science* 287(5452):451-452 (2000).

Vignali D.A.A., "Multiplexed Particle-Based Flow Cytometric Assays", *Journal of Immunological Methods* 243:243-255 (2000).

Park M.K. et al., "A Latex Bead-Based Flow Cytometric Immunoassay Capable of Simultaneous Typing of Multiple Pneumococcal Serotypes (Multibead Assay)", *Clinical and Diagnostic Laboratory Immunology* 7(3):486-489 (2000).

Bishop J.E. et al., "Simultaneous Quantification of Six Human Cytokines in a Single Sample Using Microparticle-Based Flow Cytometric Technology", *Clinical Chemistry* 45(9):1693-1694 (1999).

Chan D.W. et al., "National Academy of Clinical Biochemistry Guidelines for the Use of Tumor Markers in Ovarian Cancer", *NACB: Practice Guidelines and Recommendations for Use of Tumor Markers in the Clinic Ovarian Cancer Section* 3E:1-21 (2006).

* cited by examiner

Figure 1

| Panel | Biomarkers | Fold sample dilution | Panel | Biomarkers | Fold sample dilution |
|---|---|---|---|---|---|
| Vascular Injury Panel II | serum amyloid A (SAA) | 200x | Custom Panel 3 | Vascular endothelial growth factor (VEGF) | 1x |
| | C-reactive protein (CRP) | | | Basic fibroblast growth factor (bFGF) | |
| | Secreted intercellular adhesion molecule 1 (ICAM-1) | | | Placental growth factor (PlGF) | |
| | Vascular cell adhesion molecule 1 (VCAM-1) | | | Soluble vascular endothelial growth factor 1 (Flt-1, VEGFR-1) | |
| Custom Panel 1 | Tumor necrosis factor receptor 1 (TNFR-1) | 100x | | CA125 | |
| | Rantes | | | Osteoprotegerin (OPGN) | |
| | Interleukin 6 receptor (IL6R) | | Human Proinflammatory 9-plex | Granulocyte macrophage colony stimulating factor (GM-CSF) | 1x |
| Human Growth Factor duplex | cKit | 50x | | Interferon gamma (IFN-γ) | |
| | Soluble vascular endothelial growth factor receptor (KDR, VEGFR2) | | | Interleukin 1β (IL-1β) | |
| PICP, EGFR duplex | Human C-terminal pro-peptide of Collagen Type I (PICP) | 50x | | Interleukin 2 (IL-2) | |
| | Epidermal growth factor receptor (EGFR) | | | Interleukin 6 (IL-6) | |
| Human Bone Panel II | Osteopontin (OPN) | 20x | | Interleukin 8 (IL-8) | |
| | Osteonectin (ONN) | | | Interleukin 10 (IL-10) | |
| | Osteocalcin (OCL) | | | Interleukin 12p70 (IL-12p70) | |
| Custom Panel 2 | E-cadherin | 10x | | Tumor necrosis factor alpha (TNFα) | |
| | P-cadherin | | Chemokine | Eotaxin | |
| | Tumor necrosis factor receptor 1 (TNFR-1) | | | Eotaxin-3 | |
| | prolactin | | | Interleukin 8 (IL-8) | |
| Human MMP 3-plex | matrix metalloproteinase 2 (MMP-2) | 10x | | Interferon inducible protein 10 (IP-10) | |
| | matrix metalloproteinase 10 (MMP-10) | | | Macrophage chemoattractant protein 1 (MCP-1) | |
| | matrix metalloproteinase 1 (MMP-1) | 5x | | Macrophage chemoattractant protein 4 (MCP-4) | |
| | matrix metalloproteinase 3 (MMP-3) | | | Macrophage derived chemokine (MDC) | |
| | matrix metalloproteinase 9 (MMP-9) | | | Macrophage inflammatory protein 1β (MIP-1β) | |
| | | | | Thymus and activation-regulated chemokine (TARC) | |

Growth factors    e.g. VEGF, VEGFR, PlGF
Bone markers    e.g. osteopontin, osteoprotegerin
Cancer markers e.g. CA125, E-cadherin, P-cadherin Chemokines/cytokines   e.g. IL-6, IL-8
Inflammation markers    e.g. SAA, CRP

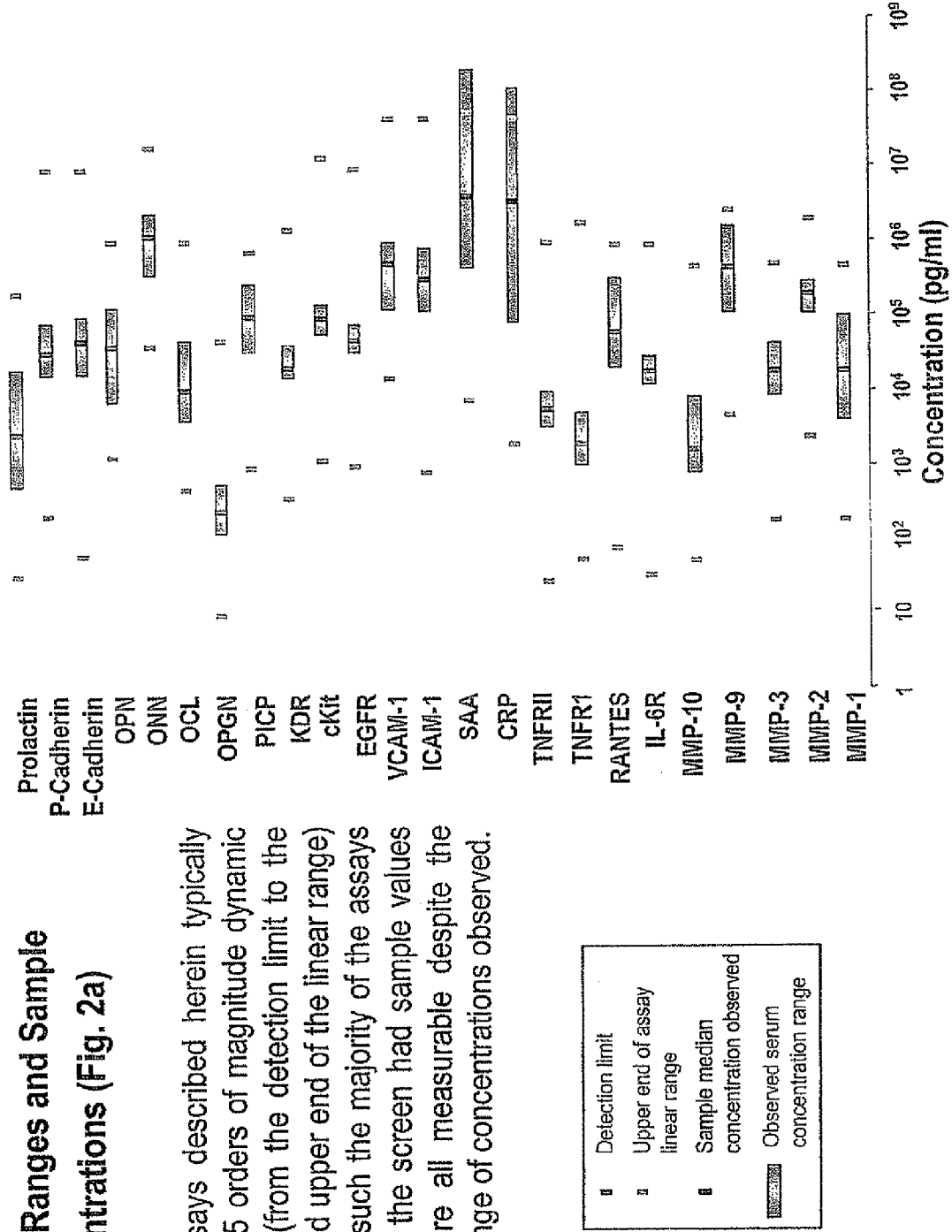
Assay Ranges and Sample Concentrations (Fig. 2a)
The assays described herein typically have 3-5 orders of magnitude dynamic ranges (from the detection limit to the observed upper end of the linear range) and as such the majority of the assays used in the screen had sample values that were all measurable despite the wide range of concentrations observed.

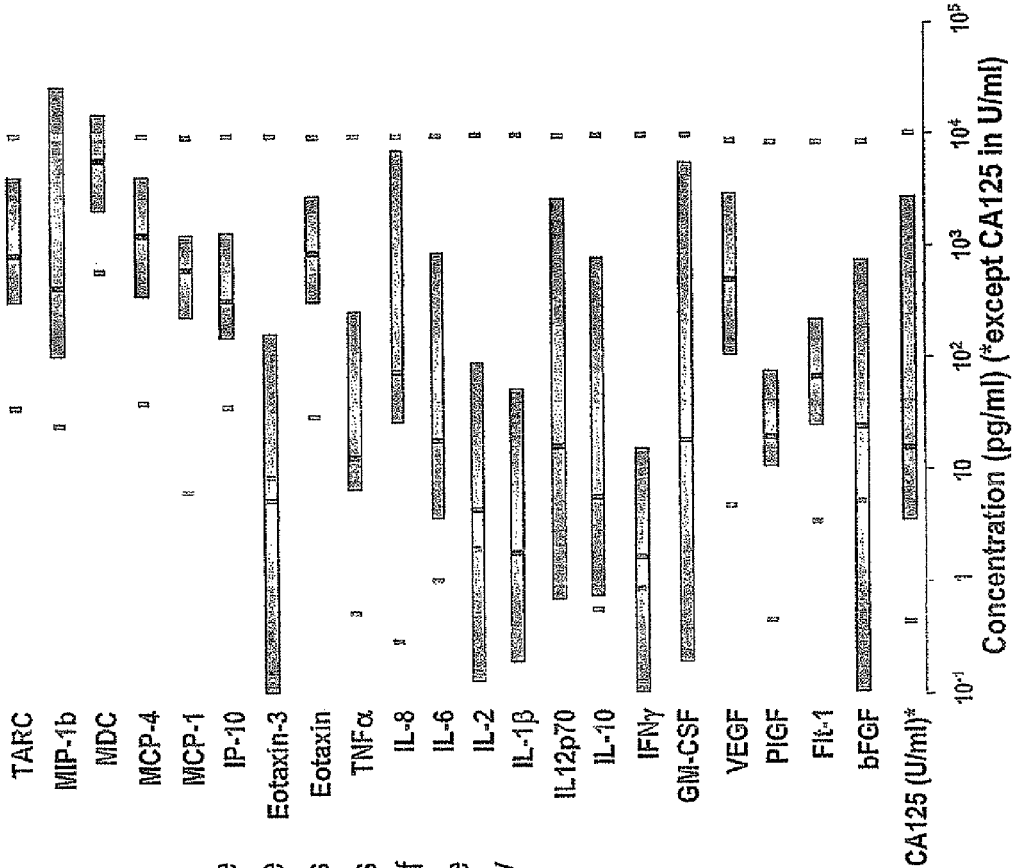
Assay Ranges and Sample Concentrations (Fig. 2b)
A few assays had some sample concentrations observed to be below the detection limits of these assays. It is apparent from the median concentrations shown, however, that the majority of sample concentrations were above the detection limits and therefore accurately measurable.

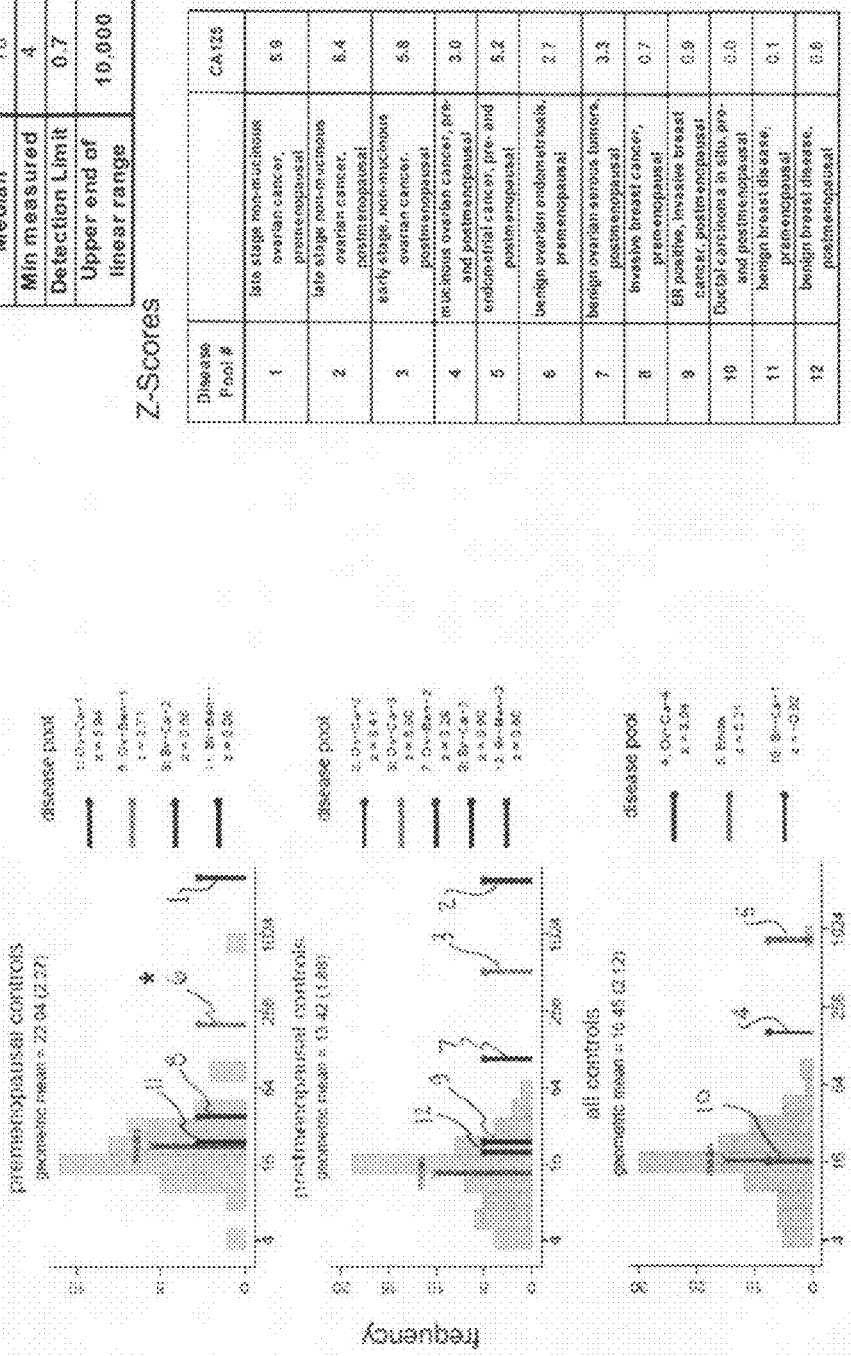

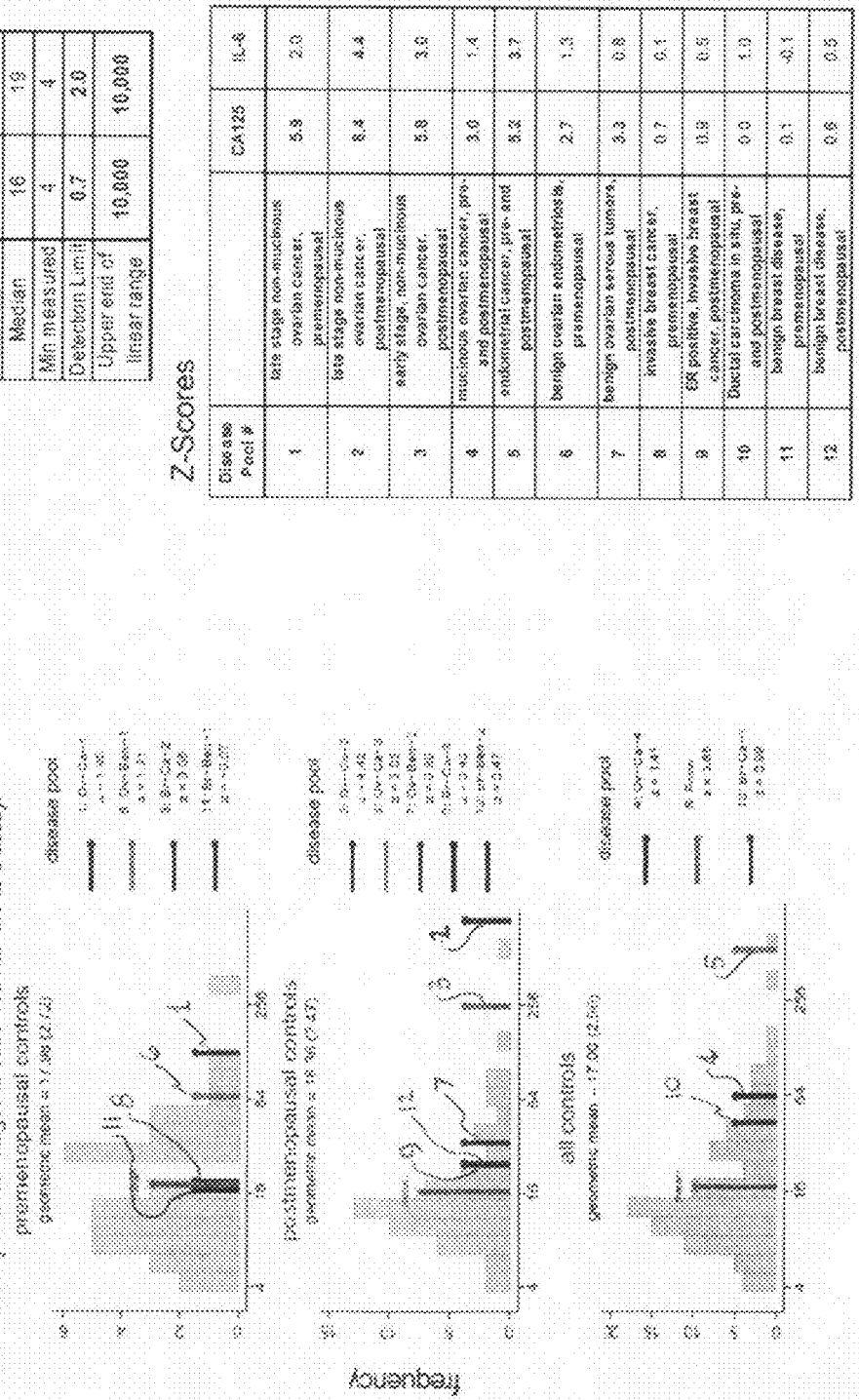

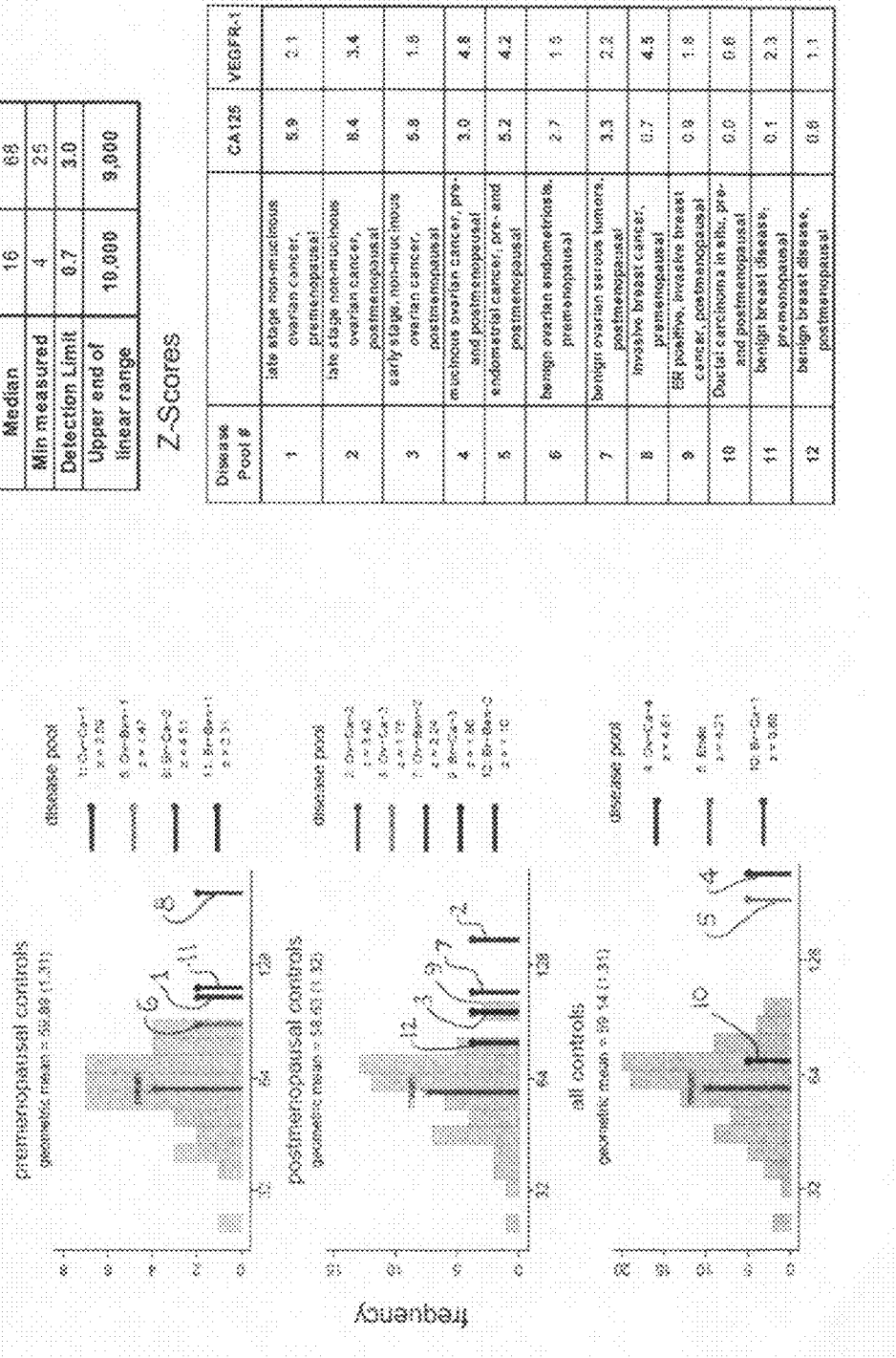

Fig. 6. Additional Markers of Interest to Ovarian and Endometrial Cancers

The performances of other markers demonstrating specific detection of pelvic conditions are summarized below in terms of Z scores, comparing to values for CA125 and IL-6. The additional markers of interest include several cytokines/chemokines (IL-1b, IL-2, IL-8, eotaxin 3), a cytokine receptor (TNFR1), inflammation markers (CRP, SAA, IL-1b, IL-8), a matrix metalloproteinase (MMP-10), an angiogenesis regulatory factor (Flt-1), and a cell adhesion molecule (P-cadherin). Serum biomarkers suggested to be of potential value as ovarian cancer diagnostic markers, osteopontin (OPN) and prolactin, did not demonstrate specific detection of ovarian cancer case pools in the current experiments.

| Pool # | | CA125 | IL-6 | Flt-1/VEGFR-1 | MMP-10 | CRP | SAA | IL-8 | IL-1b | IL-2 | P-Cadherin | Eotaxin-3 | TNFR1 | OPN | Prolactin | PIGF |
|---|---|---|---|---|---|---|---|---|---|---|---|---|---|---|---|---|
| 1 | late stage non-mucinous ovarian cancer, premenopausal | 5.9 | 2.0 | 2.1 | 1.7 | 2.1 | 2.6 | 1.4 | 0.6 | 1.1 | 2.2 | 0.8 | 1.3 | 1.5 | 1.6 | 1.9 |
| 2 | late stage non-mucinous ovarian cancer, postmenopausal | 8.4 | 4.4 | 3.4 | 4.4 | 3.5 | 4.6 | 4.2 | 3.1 | 3.5 | 3.0 | 3.4 | 2.2 | 1.2 | 2.2 | 1.2 |
| 3 | early stage, non-mucinous ovarian cancer, postmenopausal | 5.8 | 3.0 | 1.8 | 4.1 | 2.4 | 2.4 | 3.2 | 2.1 | 3.0 | 1.7 | 2.9 | 1.0 | -0.9 | 0.2 | 0.3 |
| 4 | mucinous ovarian cancer, pre- and postmenopausal | 3.0 | 1.4 | 4.8 | 1.2 | 2.1 | 3.7 | 2.1 | 1.3 | 1.9 | 2.4 | 0.8 | 1.5 | -0.2 | 2.5 | 1.6 |
| 5 | endometrial cancer, pre and postmenopausal | 5.2 | 3.7 | 4.2 | 4.1 | 2.7 | 4.3 | 3.3 | 2.3 | 2.4 | 2.7 | 2.1 | 3.4 | 0.5 | 1.9 | 1.8 |
| 6 | benign ovarian endometriosis, premenopausal | 2.7 | 1.3 | 1.5 | 0.9 | 0.5 | 0.7 | 3.0 | 1.6 | 1.8 | 0.9 | 1.2 | 0.9 | -1.4 | 0.6 | 0.5 |
| 7 | benign ovarian serous tumors, postmenopausal | 3.3 | 0.8 | 2.2 | 1.5 | 1.6 | 1.0 | 3.0 | 1.5 | 1.2 | 0.6 | 1.8 | 1.9 | -1.0 | 2.6 | 0.6 |
| 8 | Invasive breast cancer, premenopausal | 0.7 | 0.1 | 4.5 | 0.8 | 0.5 | 0.5 | -0.1 | -0.2 | -0.1 | 0.3 | -0.4 | 0.7 | -0.4 | 1.1 | 7.6 |
| 9 | ER positive, Invasive breast cancer, postmenopausal | 0.9 | 0.5 | 1.8 | 2.4 | 1.3 | 0.9 | 0.0 | 0.6 | 0.8 | 0.3 | 2.9 | 0.7 | 0.1 | 0.4 | 0.4 |
| 10 | Ductal carcinoma in situ, pre- and postmenopausal | 0.0 | 1.0 | 0.6 | 0.9 | 0.6 | 0.6 | -0.8 | -0.5 | -1.1 | 0.2 | 0.2 | 0.3 | -0.2 | 0.4 | 0.2 |
| 11 | benign breast disease, premenopausal | 0.1 | -0.1 | 2.3 | 1.0 | 0.4 | 0.4 | -0.2 | -0.7 | -0.3 | 0.5 | -0.4 | 0.7 | 0.0 | 0.2 | 2.0 |
| 12 | benign breast disease, postmenopausal | 0.6 | 0.5 | 1.1 | 1.7 | 1.6 | 1.7 | -0.8 | 0.2 | 0.5 | 0.3 | 1.1 | 0.6 | -0.4 | 1.1 | 0.6 |

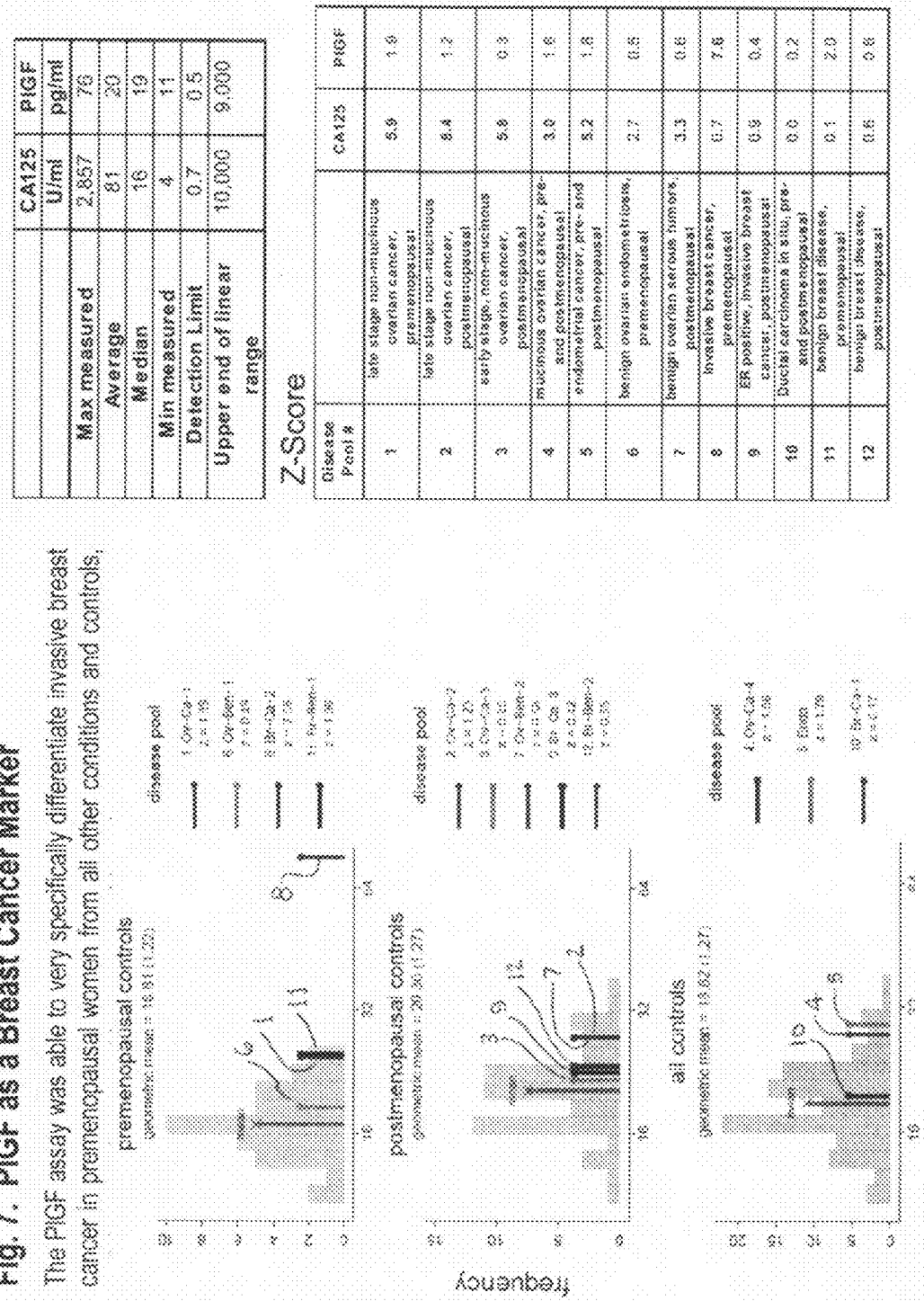

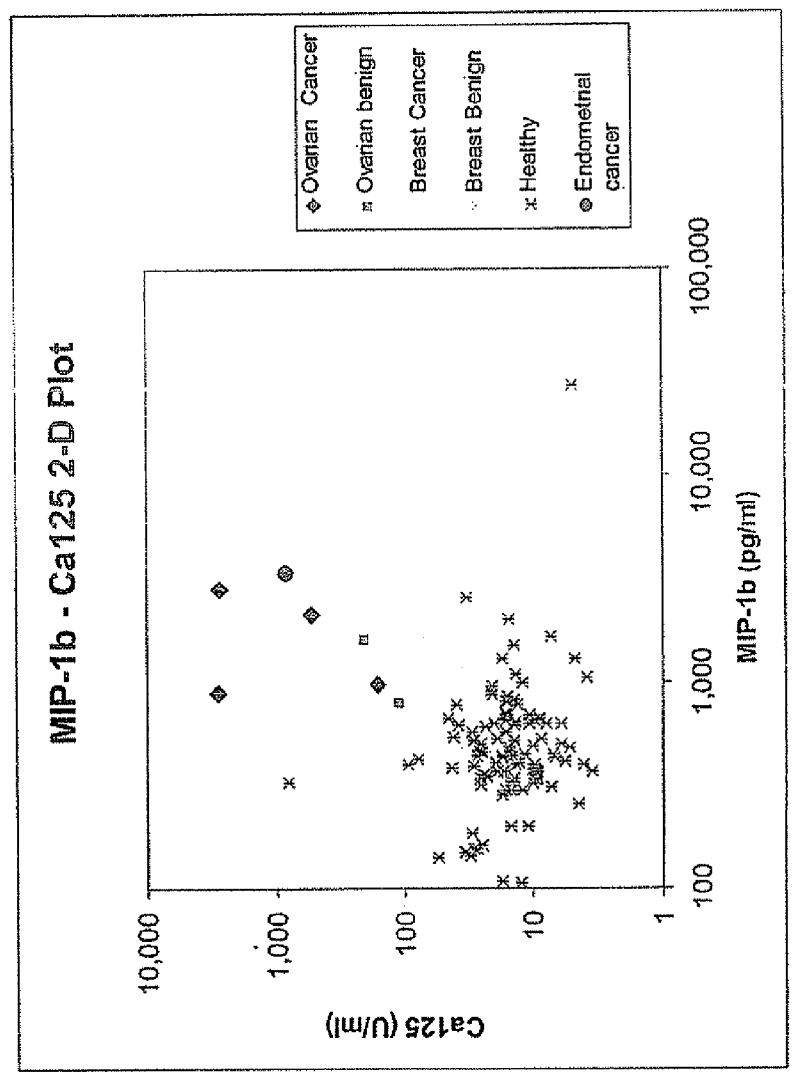

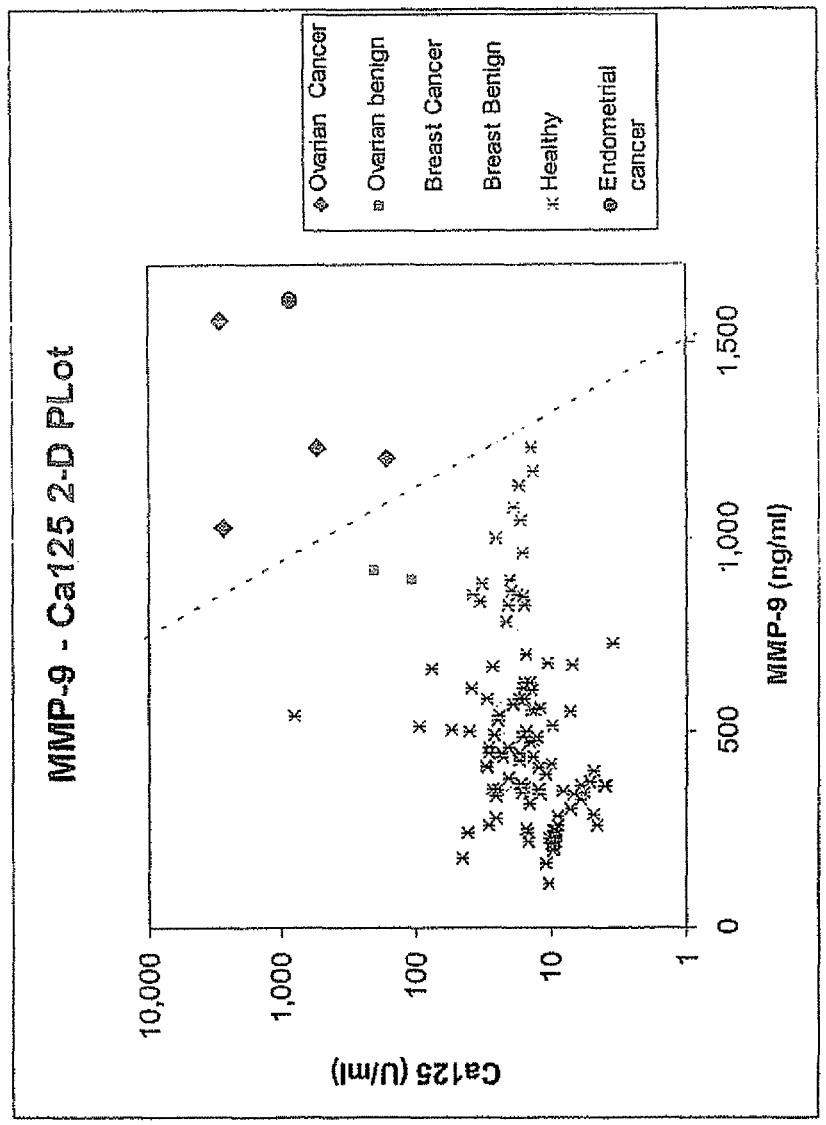

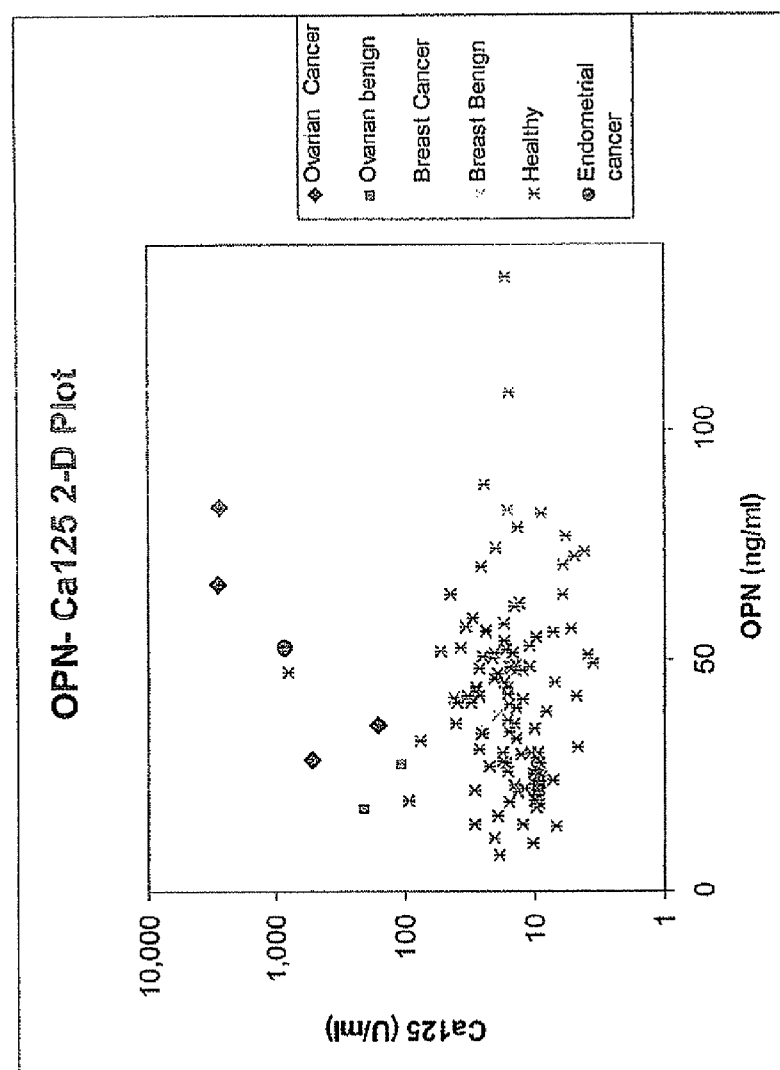

DIAGNOSTIC METHODS

CROSS REFERENCE TO RELATED APPLICATIONS

The present application claims benefit of U.S. Provisional Application No. 60/993,864 filed on Sep. 14, 2007.

FIELD OF THE INVENTION

This application relates to assay methods, modules and kits for conducting diagnostic assays useful in the detection and treatment of cancerous conditions.

BACKGROUND OF THE INVENTION

Challenges in the field of oncology include the lack of efficient means for early cancer detection and for specific cancer subtyping, which are needed for effective and specific diagnosis, targeted therapy and prognosis. The need for identification of appropriate serum biomarkers for detection of breast, ovarian, and endometrial cancers has been the impetus behind many initiatives targeting the early detection of biomarker development and the assessment of emerging technologies in this area, which are each important for development of suitable early cancer detection screening tests to reduce the mortality associated with these cancers in women.

SUMMARY OF THE INVENTION

The present invention provides a method for diagnosing a cancerous condition in a patient comprising (a) measuring a level of a first biomarker in a test sample obtained from a patient, wherein said first biomarker is selected from the group consisting of Flt1, MMP-10, PlGF, and combinations thereof; (b) diagnosing from said measuring step the presence or absence of said cancerous condition in said patient.

In one embodiment, the method further comprises measuring a level of at least one additional biomarker in said sample and determining from said level of said first biomarker and said level of said at least one additional biomarker the presence or absence of said cancerous condition in said patient. Alternatively or in an additional embodiment, the method further comprises comparing said level of said first biomarker in said sample to a level of said first biomarker in a normal control sample and diagnosing the presence or absence of said cancerous condition in said patient based on said comparison. Therefore, the method further comprises comparing said level of said first biomarker and said at least one additional biomarker(s) in said sample to a level of said first biomarker and said at least one additional biomarker(s) in a normal control sample and diagnosing the presence or absence of said cancerous condition in said patient based on said comparison.

In one embodiment, the at least one additional biomarker is selected from the group consisting of CA125, IL-6, CRP, SAA, IL-8, IL-1β, IL-2, P-Cadherin, Eotaxin-3, TNFR1, OPN, Prolactin, and combinations thereof.

The methods of the present invention may be used to diagnose and/or treat a cancerous condition selected from the group consisting of ovarian, breast, endometrial cancers, and combinations thereof. The patient may be a pre- or postmenopausal woman.

In one embodiment, the diagnosing step comprises comparing said level of said first biomarker to a detection cut-off level, wherein said first biomarker level above (or, alternatively, below) said detection cut-off level is indicative of said cancerous condition. In addition, the diagnosing step comprises comparing said level of said at least one additional biomarker to a detection cut-off level, wherein said at least one additional biomarker level above (or, alternatively, below) said detection cut-off level is indicative of said cancerous condition.

In another embodiment, the invention provides a method for monitoring the progression of a cancerous condition in a patient, said method comprising (a) measuring the level(s) of a first biomarker in samples obtained, at different times, from said patient, wherein said first biomarker is selected from the group consisting of Flt-1, MMP-10, PlF, and combinations thereof; and (b) determining from said level(s) of said first biomarker the progression or efficacy of treatment of said cancerous condition. Alternatively, the invention provides a method for evaluating the efficacy of a cancer therapeutic agent or treatment regimen in a patient that has or is suspected to have a cancerous condition, said method comprising (a) measuring the level of a first biomarker in a sample obtained from said patient, wherein said first biomarker is selected from the group consisting of Flt-1, MMP-10, PlGF, and combinations thereof; (b) measuring the level of said first biomarker in a sample of a tumor model that has been exposed to said agent or treatment regimen; and (c) comparing the levels measured in steps (a) and (b) to determine the efficacy of said agent or treatment regimen.

The invention provides an assay method wherein said measuring step is conducted on a single sample. The measuring step may also be conducted in a single assay chamber. The assay chamber may be a single well of an assay plate or a cartridge. In addition, the biomarker(s) level is measured using an immunoassay. In one embodiment, the patient sample is selected from the group consisting of blood, serum and plasma. The sample may also be selected from a group consisting of biopsy tissue, intestinal mucosa and urine.

BRIEF DESCRIPTION OF THE FIGURES

FIG. 1 is a table that summarizes the biomarkers that were analyzed in the assays of the present invention.

FIGS. 2A and 2B reflect the assay ranges and levels used in one embodiment of the assays of the present invention.

FIG. 3 shows the results obtained from one embodiment of the assays of the present invention using CA 125 as the reference biomarker.

FIG. 4 shows the results obtained from one embodiment of the assays of the present invention using IL-6 as the reference biomarker.

FIG. 5 shows the results obtained from one embodiment of the assays of the present invention using VEGFR-1 (Flt-1) as the reference biomarker.

FIG. 6 shows additional markers of interest to ovarian and endometrial cancers.

FIG. 7 shows the results obtained from one embodiment of the assays of the present invention using PlGF as a reference marker.

DETAILED DESCRIPTION OF THE INVENTION

Figure 8A:
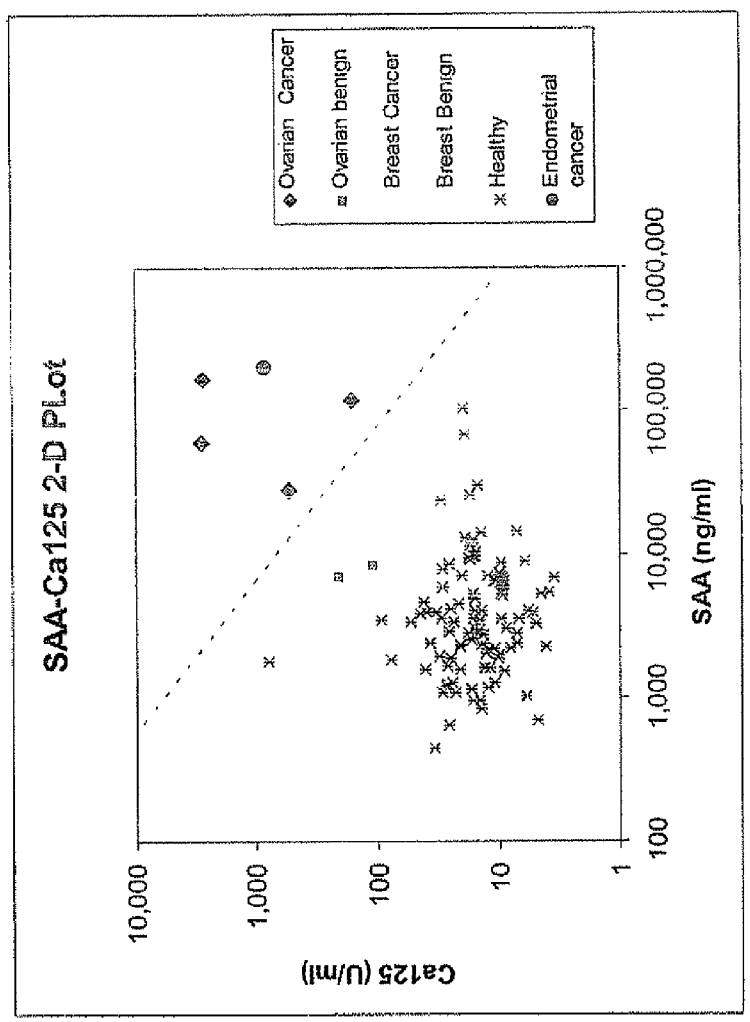
FIG. 8A to 8P provides evidence that specific combinations of biomarkers can be used to increase the confidence of cancer diagnosis.
Figure 8B:
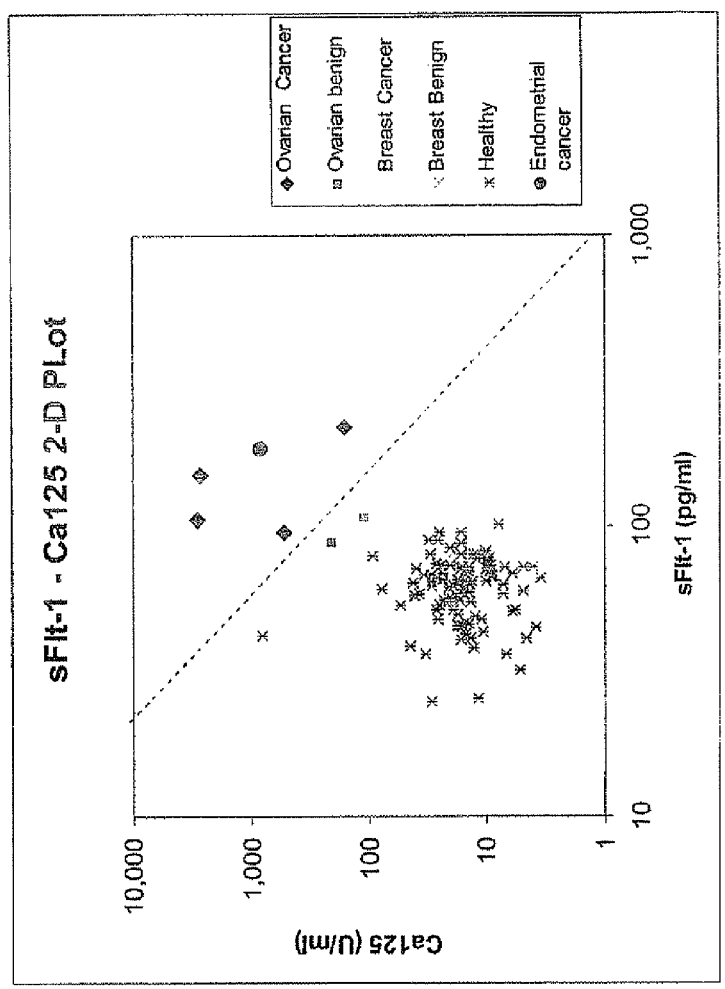
Figure 8C:
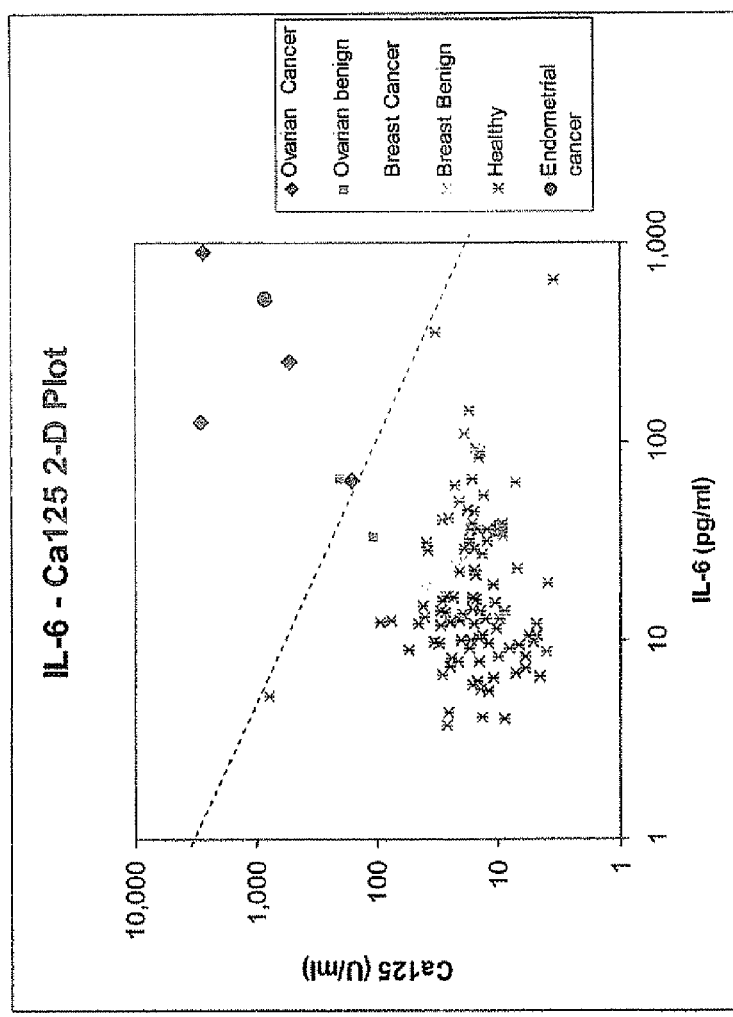
Figure 8D:
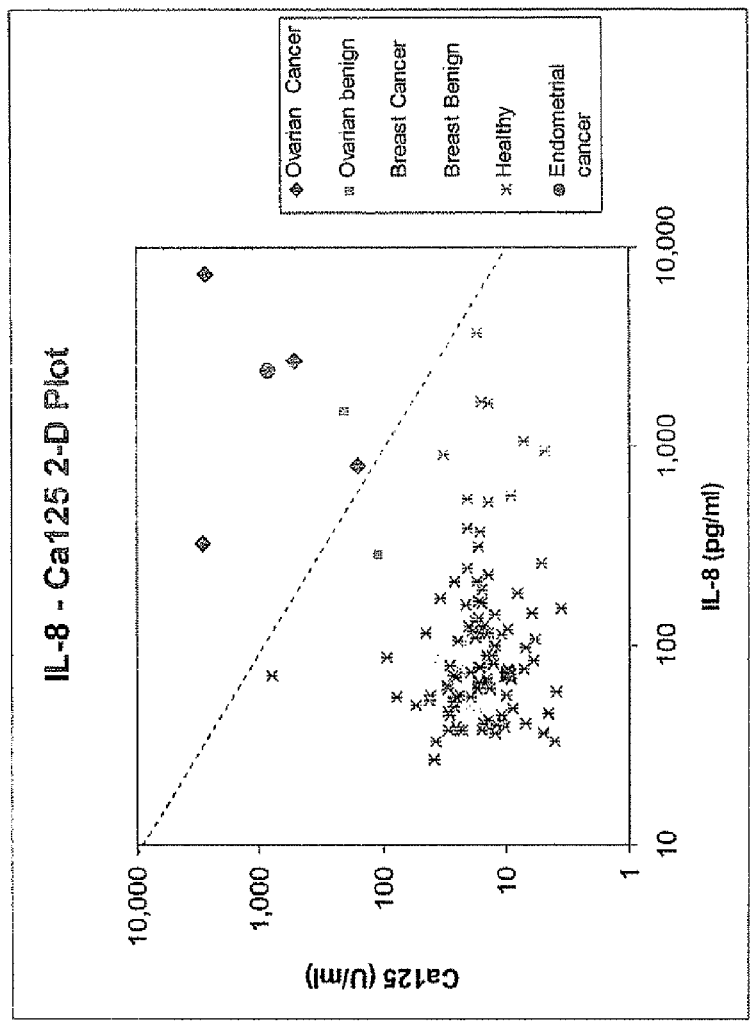
Figure 8E:
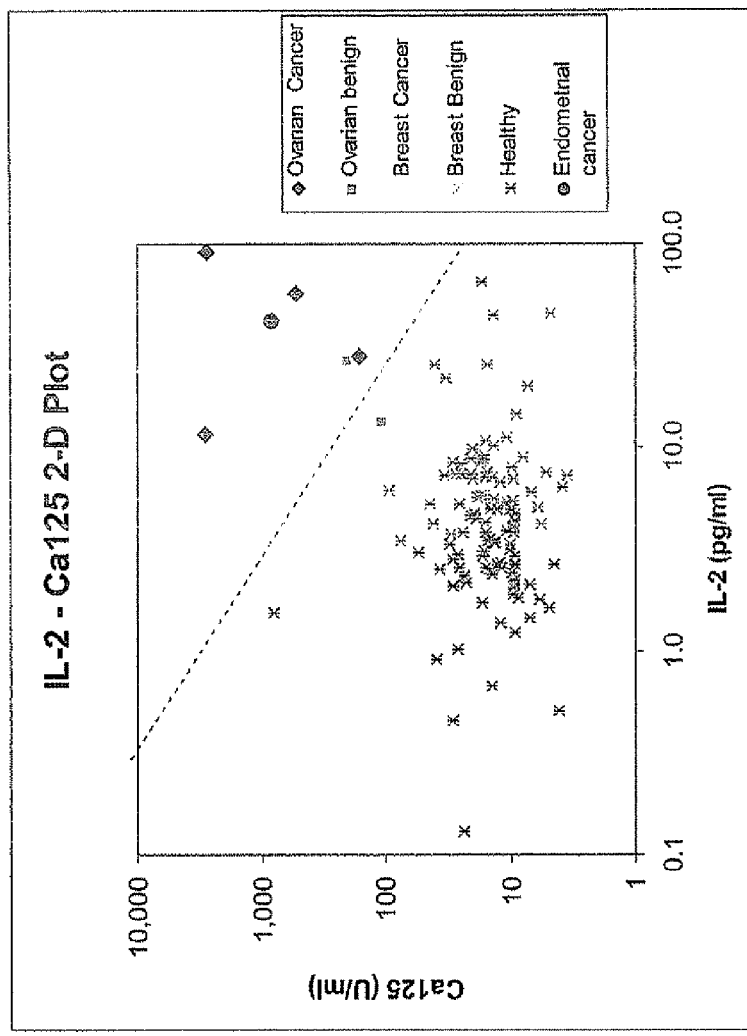
Figure 8G:
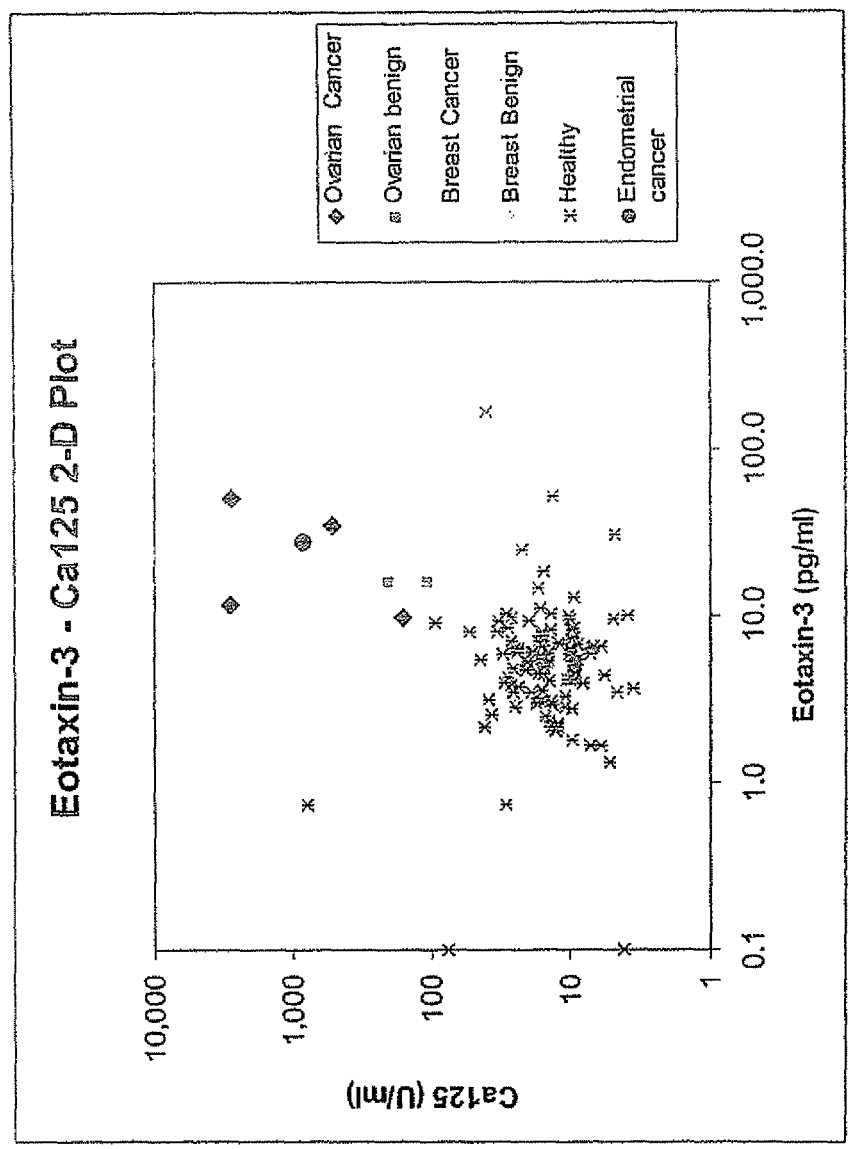
Figure 8H:
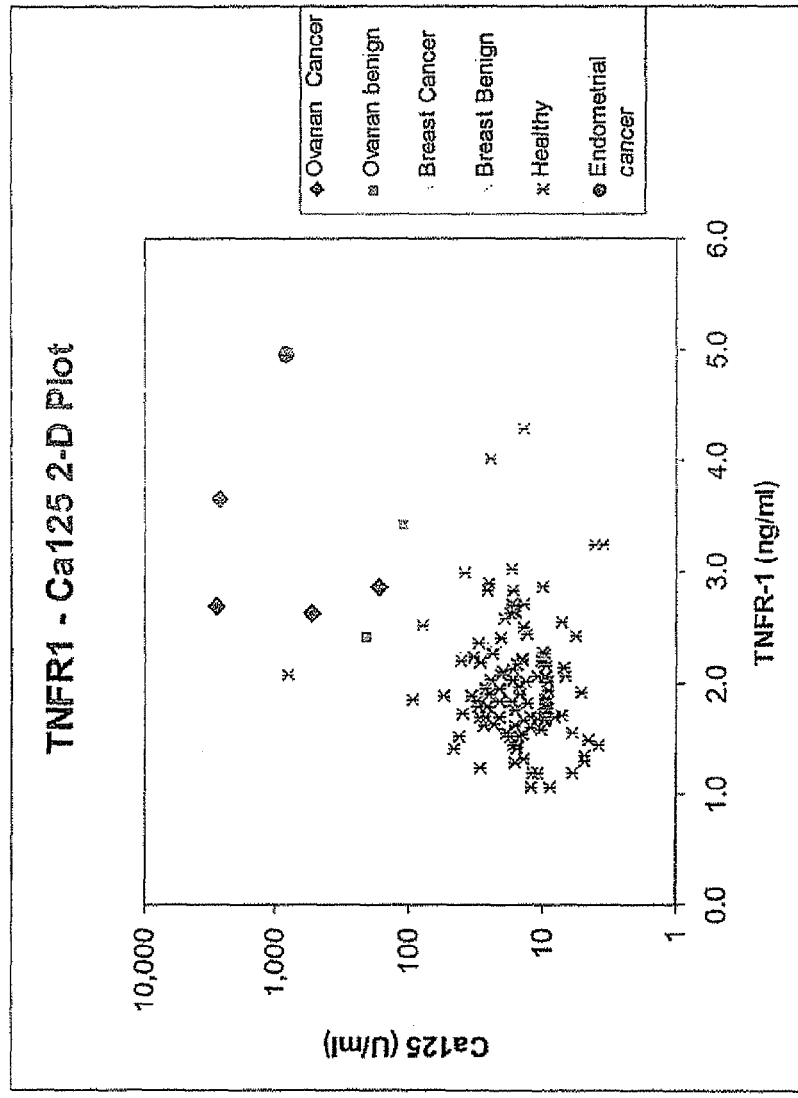
Figure 8I:
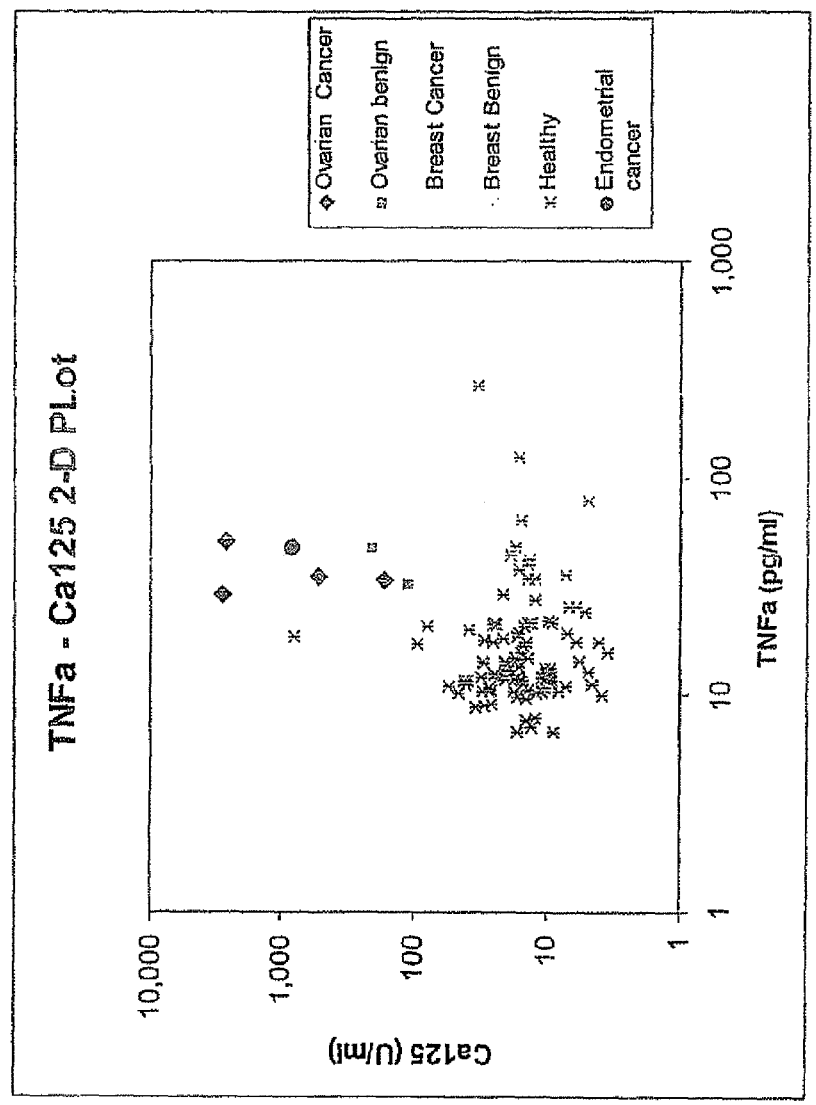
Figure 8J:
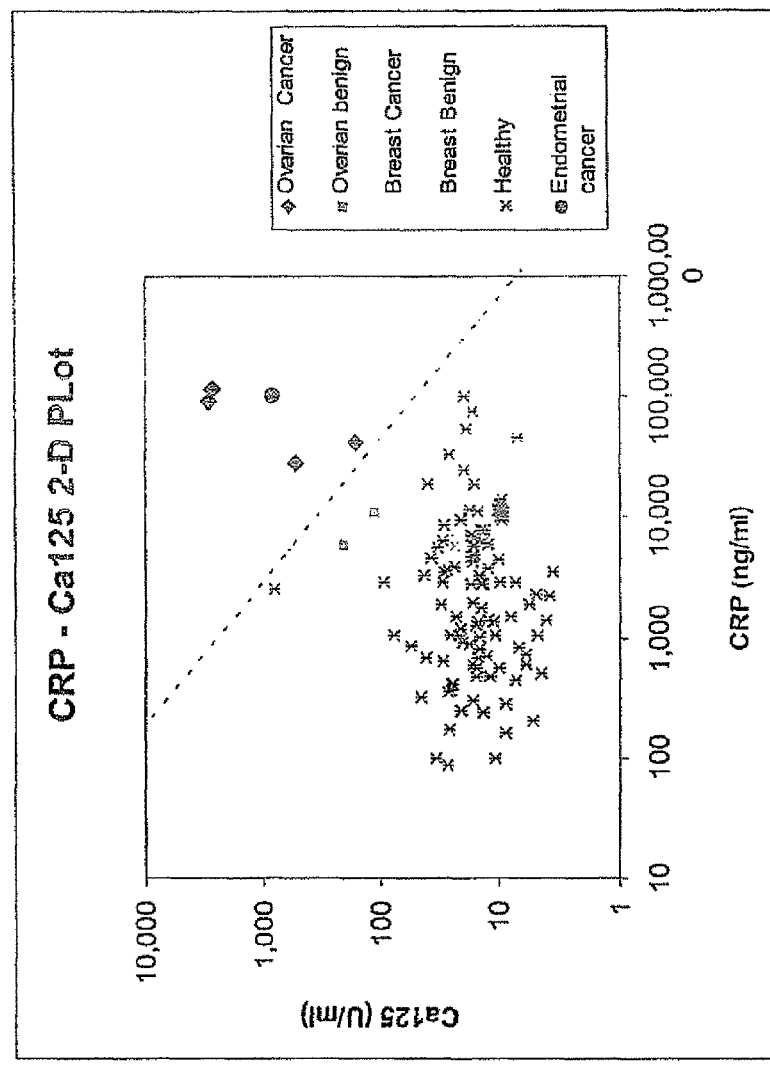
Figure 8L:
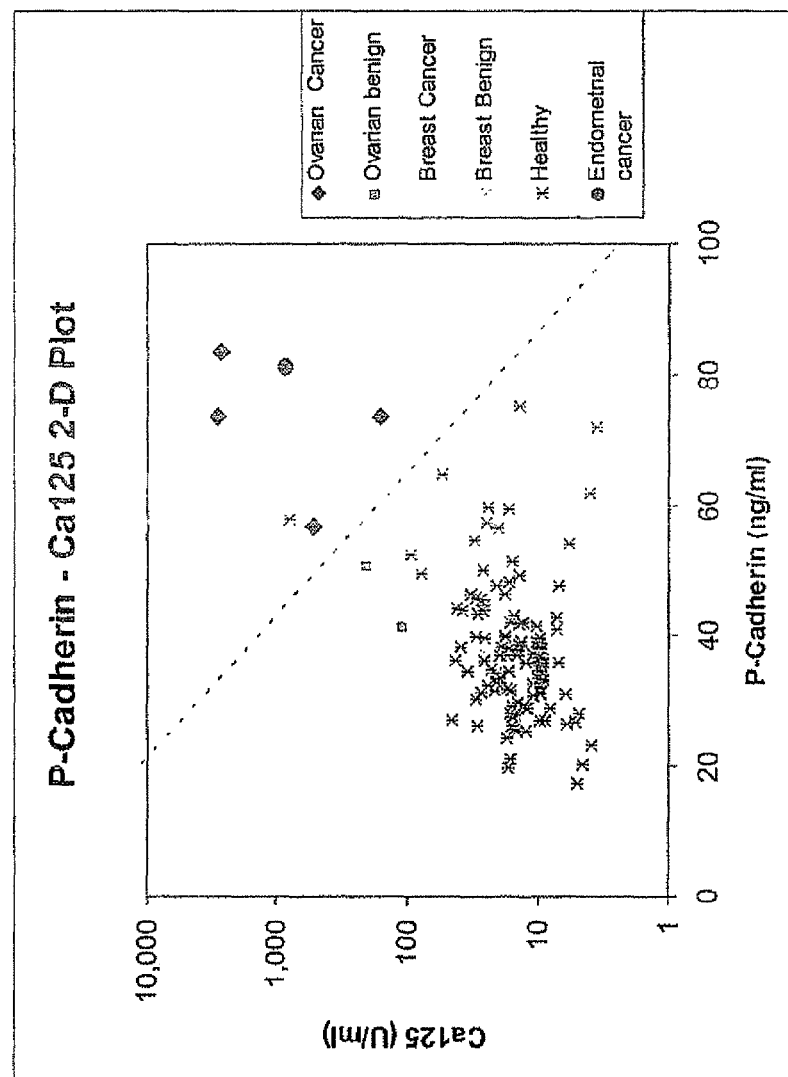
Figure 8M:
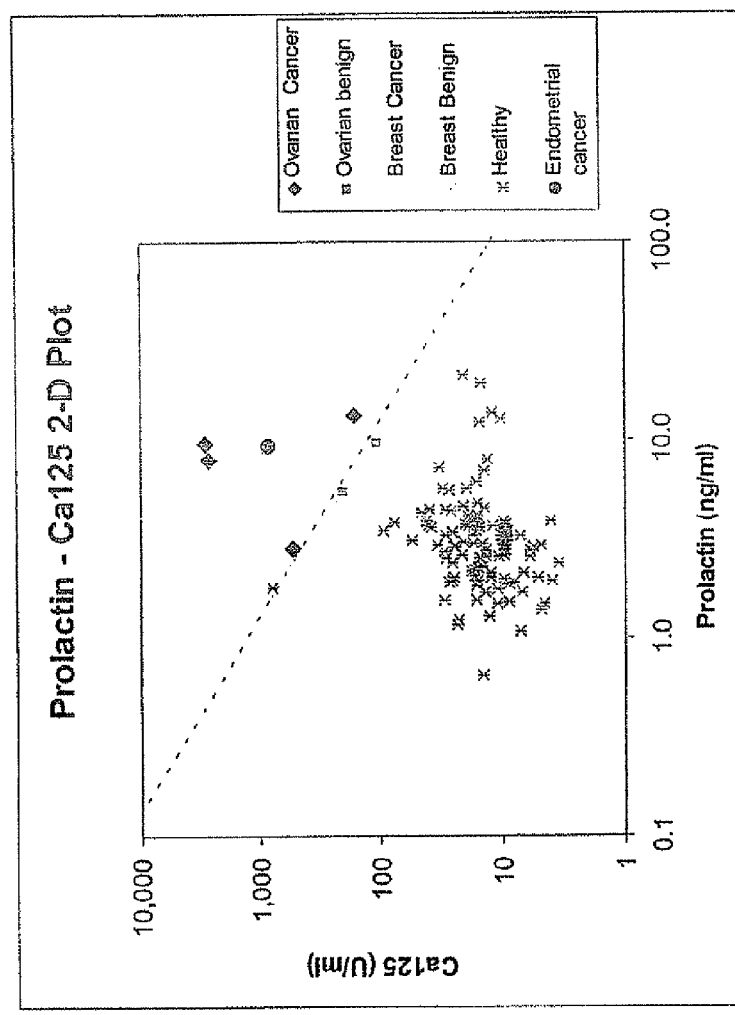
Figure 8N:
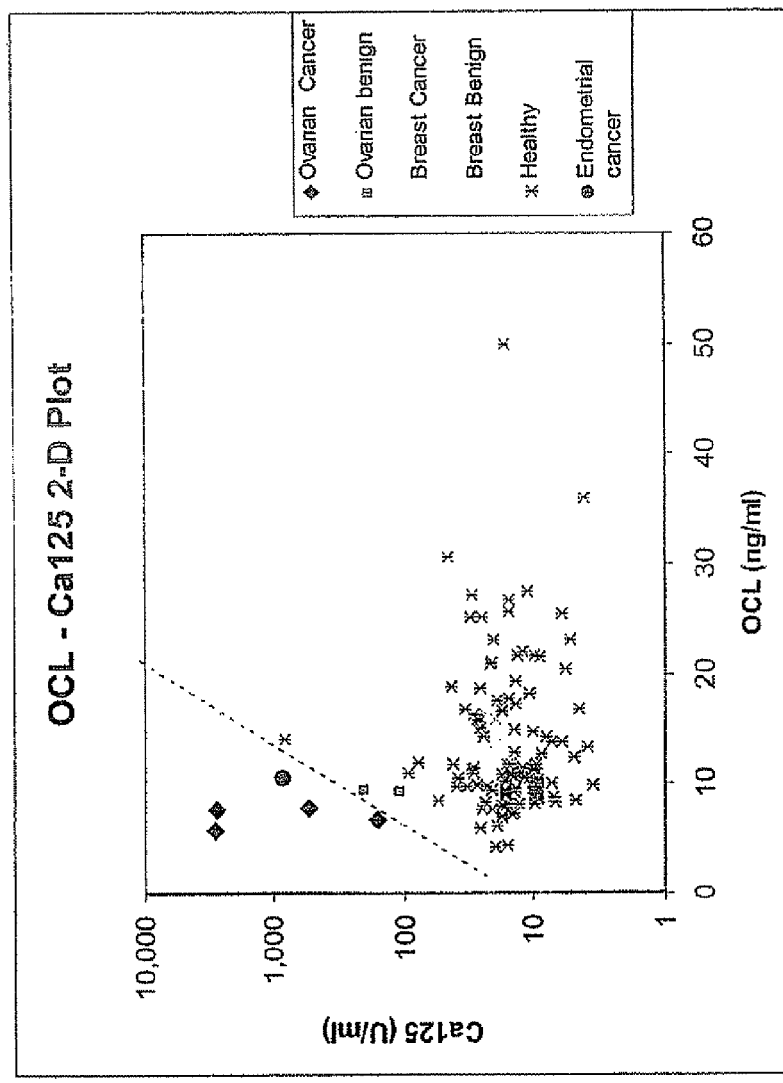
Figure 8P:
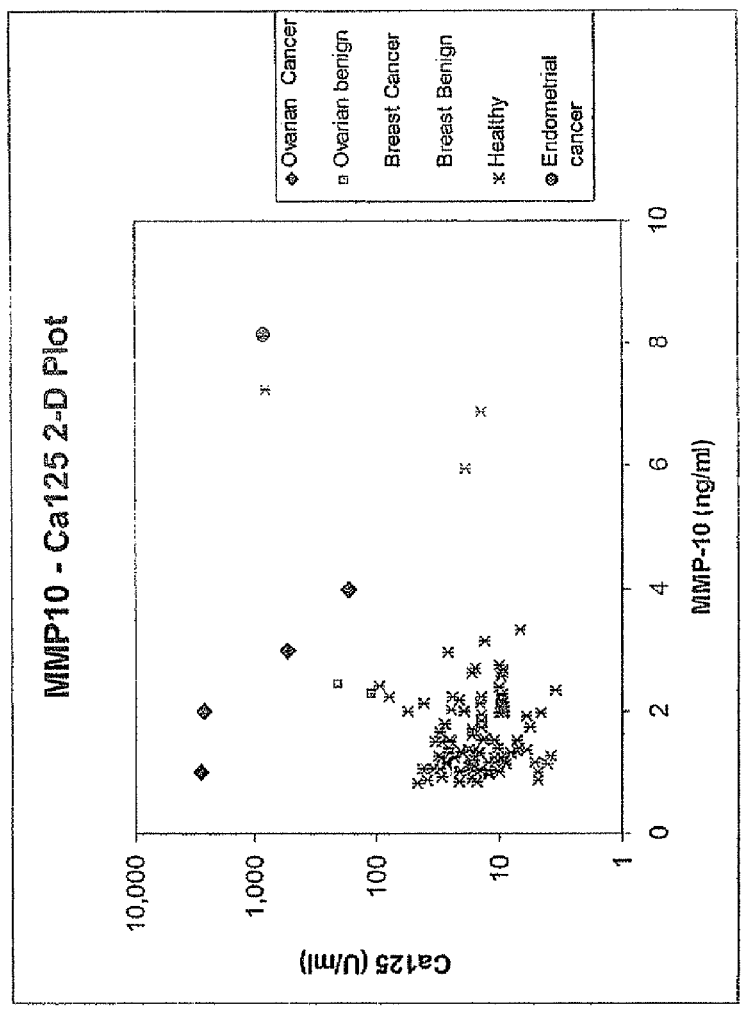

The present invention provides a method for diagnosing a cancerous condition in a patient comprising (a) measuring a level of a first biomarker in a test sample obtained from a patient, wherein said first biomarker is selected from the group consisting of Flt1, MMP-10, PlGF, and combinations thereof; and (b) diagnosing from said measuring step the presence or absence of said cancerous condition in said patient Therefore in one embodiment, the invention provides a method of diagnosing a cancerous condition in a patient by measuring a level of Flt-1 and diagnosing the patient for the presence or absence of the cancerous condition by identifying the level of Flt-1 in the patient sample. Similarly, the invention provides embodiments in which the level of MMP-10, and/or PlGF is measured in the patient sample and based on this biomarker level, the patient is diagnosed with the cancerous condition. In an alternative embodiment, Flt-1 and MMP-10 are analyzed in a single assay, Flt-1 and PlGF are analyzed in a single assay, MMP-10 and PlGF are analyzed in a single assay, and/or Flt-1, MMP-10 and PlGF are analyzed in a single assay.

The invention also contemplates a diagnostic method as described above, wherein one or more of Flt-1, MMP-10, and/or PlGF are analyzed in a single assay, and the level of at least one additional biomarker is measured in the sample. Therefore, the levels of the first biomarker and the additional biomarker(s) in the test sample may be used to diagnose a cancerous condition in a patient In a preferred embodiment, the additional biomarker is selected from CA125, IL-6, CRP, SAA, IL-8, IL-1β, IL-2, PC-Cadherin, Eotaxin-3, TNFR1, OPN, Prolactin, and combinations thereof. Other biomarkers are known and may be used in combination with the methods of the present invention, including and not limited to VEGF, PDGF, focal adhesion kinase, AKT, erb-B, HER2/neu, Trk, other matrix metalloproteinases, and combinations thereof.

In one embodiment of the present invention, the level of the first biomarker and/or the level of the additional biomarkers in the test sample are compared to the levels of these biomarkers in a corresponding normal control sample. The difference between the normal control sample biomarker levels and that of the test sample may be the basis for diagnosing a cancerous condition in a patient. Alternatively, the method of the invention contemplates a comparison of the level of the first biomarker to a detection cut-off level, wherein the first biomarker level above or below the detection cut-off level is indicative of the cancerous condition. In addition, the diagnostic methods of the invention also contemplate comparing the level of the at least one additional biomarker to a detection cut-off level, wherein the at least one additional biomarker level above or below the detection cut-off level is indicative of the cancerous condition.

The diagnostic methods of the present invention may be used to diagnose a variety of cancerous conditions, including but not limited to ovarian, breast, endometrial cancers, cervical cancers, uterine cancers and combinations thereof. In addition, the diagnostic methods of the present invention may be used to identify endometriosis. These methods may be used to identify cancerous conditions in a patient, e.g., in a pre- or post-menopausal woman. As used herein, the term "cancer" is intended to mean a class of diseases characterized by the uncontrolled growth of aberrant cells, including all known cancers, and neoplastic conditions, whether characterized as malignant, benign, soft tissue or solid tumor. In some embodiments of the invention, the assay may have diagnostic value irrespective of the menopausal state of a female patient. In other embodiments, the diagnostic value is higher (or lower) in selected subpopulations, e.g., pre- or post-menopausal women.

The methods of the present invention may also be used to monitor the progression of a cancerous condition in a patient by (a) measuring the level(s) of a first biomarker in samples obtained, at different times, from said patient, wherein said first biomarker is selected from the group consisting of Flt-1, MMP-10, PlGF, and combinations thereof; and (b) determining from said level(s) of said first biomarker the progression or efficacy of treatment of said cancerous condition. In one embodiment, the method of the present invention may be used to differentiate between the presence or absence of different cancer subtypes in a sample taken from a patient.

Alternatively, the methods of the present invention may be used to evaluate the efficacy of a cancer therapeutic agent or treatment regimen in a patient that has or is suspected to have a cancerous condition, said method comprising (a) measuring the level of a first biomarker in a sample obtained from said patient, wherein said first biomarker is selected from the group consisting of Flt-1, MMP-10, PlGF, and combinations thereof, (b) measuring the level of said first biomarker in a sample of a tumor model that has been exposed to said agent or treatment regimen; and (c) comparing the levels measured in steps (a) and (b) to determine the efficacy of said agent or treatment regimen. The methods of the present invention may also be used to select a treatment regimen or to adjust the dose of one or more components in a therapeutic treatment regimen. It may also be used to evaluate whether any supportive or palliative care therapies should be included in a treatment regimen, and in that regard, the skilled artisan may include additional biomarkers in the methods of the invention.

The assays of the present invention may be conducted by any suitable method. In one embodiment, the measuring step is conducted on a single sample, and it may also be conducted in a single assay chamber, including but not limited to a single well of an assay plate. The assay chamber may also be an assay chamber of a cartridge.

As used herein, the term "sample" is intended to mean any biological fluid, cell, tissue, organ or combinations or portions thereof, which includes or potentially includes a biomarker of a disease of interest For example, a sample can be a histologic section of a specimen obtained by biopsy, or cells that are placed in or adapted to tissue culture. A sample further can be a subcellular fraction or extract, or a crude or substantially pure nucleic acid molecule or protein preparation. In one embodiment, the samples that may be analyzed in the assays of the present invention include but are not limited to blood or blood fractions such as, serum and plasma. The sample may also include biopsy tissue, intestinal mucosa and urine. In one embodiment, the level is measured using an immunoassay.

As used herein, a "biomarker" is a substance that is associated with a particular disease. A change in the expression levels of a biomarker may correlate with the risk or progression of a disease or with the susceptibility of the disease to a given treatment A biomarker may be useful in the diagnosis of disease risk or the presence of disease in an individual, or to tailor treatments for the disease in an individual (choices of drug treatment or administration regimes). In evaluating potential drug therapies, a biomarker may be used as a surrogate for a natural endpoint such as survival or irreversible morbidity. If a treatment alters a biomarker that has a direct connection to improved health, the biomarker serves as a "surrogate endpoint" for evaluating clinical benefit A sample that is assayed in the diagnostic methods of the present invention may be obtained from any suitable patient, including but not limited to a patient suspected of having cancer or a patient having a predisposition to a cancerous condition. The patient may or may not exhibit symptoms associated with a cancerous condition.

As used herein, the term "level" refers to mean the amount, concentration, accumulation or rate of a biomarker molecule. A level can be represented, for example, by the amount or synthesis rate of messenger RNA (mRNA) encoded by a gene, the amount or synthesis rate of polypeptide corresponding to a given amino acid sequence encoded by a gene, or the amount or synthesis rate of a biochemical form of a molecule accumulated in a cell, including, for example, the amount of particular post-synthetic modifications of a molecule such as a polypeptide, nucleic acid or small molecule. The term can be used to refer to an absolute amount of a molecule in a sample or to a relative amount of the molecule, including amount or concentration determined under steady-state or non-steady-state conditions. Level may also refer to an assay signal that correlates with the amount, concentration, accumulation or rate of change of a biomarker molecule. The expression level of a molecule can be determined relative to a control molecule in a sample.

According to one aspect of the invention, the levels or levels of biomarker(s) are measured in the samples collected from individuals clinically diagnosed with or suspected of or at risk of developing cancer or a cancerous or pre-cancerous condition using conventional methods, e.g., biopsy or other conventional diagnostic methods, as well as from healthy individuals. It may also be used to screen for disease in a broad population of asymptomatic individuals. For example, specific biomarkers valuable in distinguishing between normal and diseased patients could be identified by visual inspection of the data, for example, data plotted on a one-dimensional or multidimensional graph, or using methods of statistical analysis, such as a statistically weighted difference between control individuals and diseased patients and/or Receiver Operating Characteristic (ROC) curve analysis.

For example and without limitation, diagnostically valuable biomarkers may be first identified using a statistically weighted difference between control individuals and diseased patients, calculated as $$\frac{D-N}{\sqrt{\sigma_D * \sigma_N}}$$

wherein D is the median level of a biomarker in patients diagnosed as having, for example, breast cancer or ovarian cancer, N is the median of the control individuals, $\sigma_D$ is the standard deviation of D and ($\sigma_N$ is the standard deviation of N. The larger the magnitude, the greater the statistical difference between the diseased and normal populations.

According to one embodiment of the invention, biomarkers resulting in a statistically weighted difference between control individuals and diseased patients of greater than, e.g., 1, 1.5, 2, 2.5 or 3 could be identified as diagnostically valuable markers.

Another method of statistical analysis for identifying biomarkers is the use of z-scores, e.g., as described in Skates et al (2007) Cancer Epidemiol Biomarkers Prev. 16(2):334-341.

Another method of statistical analysis that can be useful in the inventive methods of the invention for determining the efficacy of particular candidate analytes, such as particular biomarkers, for acting as diagnostic marker(s) is ROC curve analysis. An ROC curve is a graphical approach to looking at the effect of a cut-off criterion, e.g., a cut-off value for a diagnostic indicator such as an assay signal or the level of an analyte in a sample, on the ability of a diagnostic to correctly identify positive or negative samples or subjects. One axis of the ROC curve is the true positive rate (TPR, i.e., the probability that a true positive sample/subject will be correctly identified as positive, or alternatively, the false negative rate (FNR=1−TPR, the probability that a true positive sample/subject will be incorrectly identified as a negative). The other axis is the true negative rate, i.e., TNR, the probability that a true negative sample will be correctly identified as a negative, or alternatively, the false positive rate (FPR=1−TNR, the probability that a true negative sample will be incorrectly identified as positive). The ROC curve is generated using assay results for a population of samples/subjects by varying the diagnostic cut-off value used to identify samples/subjects as positive or negative and plotting calculated values of TPR or FNR and TNR or FPR for each cut-off value. The area under the curve (referred to herein as the ROC area) is one indication of the ability of the diagnostic to separate positive and negative samples/subjects.

Diagnostic indicators analyzed by ROC curve analysis may be a level of an analyte, e.g., a biomarker, or an assay signal. Alternatively, the diagnostic indicator may be a function of multiple measured values, for example, a function of the level/assay signal of a plurality of analytes, e.g., a plurality of biomarkers, or a function that combines the level or level or assay signal of one or more analytes with a patients scoring value that is determined based on visual, radiological and/or histological evaluation of a patient. The multi-parameter analysis may provide more accurate diagnosis relative to analysis of a single marker.

Candidates for a multi-analyte panel could be selected by using criteria such as individual analyte ROC areas, median difference between groups normalized by geometric inter-quartile range (IQR) etc. The objective is to partition the analyte space to improve separation between groups (for example, normal and disease populations) or to minimize the misclassification rate.

One approach is to define a panel response as a weighted combination of individual analytes and then compute an objective function like ROC area, product of sensitivity and specificity, etc. See e.g., WO 2004/058055, as well as US2006/0205012, the disclosures of which are incorporated herein by reference in their entireties.

Biomarker levels may be measured using any of a number of techniques available to the person of ordinary skill in the art, e.g., direct physical measurements (e.g., mass spectrometry) or binding assays (e.g., immunoassays, agglutination assays and immunochromatographic assays). The method may also comprise measuring a signal that results from a chemical reactions, e.g., a change in optical absorbance, a change in fluorescence, the generation of chemiluminescence or electrochemiluminescence, a change in reflectivity, refractive index or light scattering, the accumulation or release of detectable labels from the surface, the oxidation or reduction or redox species, an electrical current or potential, changes in magnetic fields, etc. Suitable detection techniques may detect binding events by measuring the participation of labeled binding reagents through the measurement of the labels via their photoluminescence (e.g., via measurement of fluorescence, time-resolved fluorescence, evanescent wave fluorescence, up-converting phosphors, multi-photon fluorescence, etc.), chemiluminescence, electrochemiluminescence, light scattering, optical absorbance, radioactivity, magnetic fields, enzymatic activity (e.g., by measuring enzyme activity through enzymatic reactions that cause changes in optical absorbance or fluorescence or cause the emission of chemi-luminescence). Alternatively, detection techniques may be used that do not require the use of labels, e.g., techniques based on measuring mass (e.g., surface acoustic wave measurements), refractive index (e.g., surface plasmon resonance measurements), or the inherent luminescence of an analyte.

Binding assays for measuring biomarker levels may use solid phase or homogenous formats. Suitable assay methods include sandwich or competitive binding assays. Examples of sandwich immunoassays are described in U.S. Pat. Nos. 4,168,146 and 4,366,241, both of which are incorporated herein by reference in their entireties. Examples of competitive immunoassays include those disclosed in U.S. Pat. Nos. 4,235,601; 4,442,204 and 5,208,535, each of which are incorporated herein by reference in their entireties.

Multiple biomarkers may be measured using a multiplexed assay format, e.g., multiplexing through the use of binding reagent arrays, multiplexing using spectral discrimination of labels, multiplexing of flow cytometric analysis of binding assays carried out on particles, e.g., using the Luminex® system. Suitable multiplexing methods include array based binding assays using patterned arrays of immobilized antibodies directed against the biomarkers of interest. Various approaches for conducting multiplexed assays have been described (See e.g., US 20040022677; US 20050052646; US 20030207290; US 20030113713; US 20050142033; and US 20040189311, each of which is incorporated herein by reference in their entireties. One approach to multiplexing binding assays involves the use of patterned arrays of binding reagents, e.g., U.S. Pat. Nos. 5,807,522 and 6,110,426; Delehanty J-B., Printing functional protein microarrays using piezoelectric capillaries, Methods Mol. Bioi (2004) 278: 135-44; Lue R Y et al., Site-specific immobilization of biotinylated proteins for protein microarray analysis, Methods Mol. Biol. (2004) 278: 85-100; Lovett, Toxicogenomics: Toxicologists Brace for Genomics Revolution, Science (2000) 289: 536-537; Berns A, Cancer: Gene expression in diagnosis, nature (2000),403,491-92; Walt, Molecular Biology: Bead-based Fiber-Optic Arrays, Science (2000) 287: 451-52for more details). Another approach involves the use of binding reagents coated on beads that can be individually identified and interrogated. See e.g., WO 9926067, which describes the use of magnetic particles that vary in size to assay multiple analytes; particles belonging to different distinct size ranges are used to assay different analytes. The particles are designed to be distinguished and individually interrogated by flow cytometry. Vignali has described a multiplex biding assay in which 64 different bead sets of microparticles are employed, each having a uniform and distinct proportion of two dyes (Vignali, D. A A, "Multiplexed Particle-Based Flow Cytometric Assays" J. Immunol. Meth. (2000) 243: 243-55). A similar approach involving a set of 15 different beads of differing size and fluorescence has been disclosed as useful for simultaneous typing of multiple pneumococcal serotypes (Park, M.K et al., "A Latex Bead-Based Flow Cytometric Immunoassay Capable of Simultaneous Typing of Multiple Pneumococcal Serotypes (Multibead Assay)" Clin. Diagn. Lab Immunol (2000) 7(3): 486-489. Bishop, J.E. et al. have described a multiplex sandwich assay for simultaneous quantification of six human cytokines (Bishop, L.E. et al., "Simultaneous Quantification of Six Human Cytokines in a Single Sample Using Microparticle-based Flow Cytometric Technology," Clin. Chem (1999) 45:1693-1694.

A diagnostic test may be conducted in a single assay chamber, such as a single well of an assay plate or an assay chamber that is an assay chamber of a cartridge. The assay modules, e.g., assay plates or cartridges or multi-well assay plates), methods and apparatuses for conducting assay measurements suitable for the present invention are described for example, in US 20040022677; US 20050052646; US 20050142033; US 20040189311, each of which is incorporated herein by reference in their entireties. Assay plates and plate readers are now commercially available (MULTISPOT® and MULTI-ARRAY® plates and SECTOR® instruments, Meso Scale Discovery®, a division of Meso Scale Diagnostics, LLC, Gaithersburg, Md.).

The following non-limiting examples serve to illustrate rather than limit the present invention.

EXAMPLES

Example 1

One hundred twenty seven serum samples were collected which consisted of 20 replicates of a normal serum pool, 95 individual controls (from 39 pre- and 56 postmenopausal women), and 12 gynecological and breast disease pools, as outlined in Table 1 below:

1. Premenopausal women with late stage, non-mucinous ovarian cancer (35)
2. Postmenopausal women with late stage, non-mucinous ovarian cancer (39)
3. Postmenopausal women with early stage, non-mucinous ovarian cancer (35)
4. Pre/postmenopausal women with mucinous ovarian cancer (35)
5. Pre/postmenopausal women with endometrial cancer (12)
6. Premenopausal women with endometriosis (38)
7. Postmenopausal women with benign serous ovarian tumors (35)
8. Premenopausal women with invasive breast cancer (43)
9. Postmenopausal women with estrogen receptor positive invasive breast cancer (36)
10. Pre/postmenopausal women with DCIS (43)
11. Premenopausal women with benign breast disease (45)
12. Postmenopausal women with benign breast disease (45)

Each sample in Table 1 was analyzed using the following assay protocol: first, a Multi-Spot® assay plate, e.g., a −24, −96, or −384 well multi-spot plate was blocked for 1 hour using a suitable blocking solution, and subsequently washed using a washing buffer. Twenty five ul assay diluent were added to each well, followed by 25 ul calibrator or sample (undiluted or diluted) to each well of the multi-spot assay plate. The plate was incubated with shaking for about 2 hours, and washed. Twenty five ul labeled antibody solution was added to each well and the plate was incubated with shaking for 1 to 2 hour, and subsequently washed. One hundred fifty ul reading buffer was added to each well and the plate was read using an MSD plate reader.

Eleven assay panels were used, measuring 46 different biomarkers using a single 0.3 ml serum aliquot. The samples were used at the dilutions indicated (typically 25 mL per well of 1 to 200-fold diluted sera). Each of the biomarkers analyzed are summarized in the table in FIG. 1. FIGS. 2A and 2B compare the dynamic range of each immunoassay to the range of concentrations measured in the sample set.

Data were analyzed by calculating the following elements:
(a) Assay detection limits were calculated;
(b) The upper end of the linear calibration ranges were estimated from the calibration curves, or the highest calibrator level used was noted, whichever was lower;

(c) The mean serum levels of the biomarkers were calculated from the duplicate sample measurements. Average and median CVs for the duplicate sample measurements were 11% and 8%, respectively;

(d) Overall average and median biomarker levels for all 127 samples were determined; and (e) The maximum serum level observed and the minimum measurable sample level were noted.

The data from each sample were then analyzed and reported as follows:

(a) Plots of the case pool values against the relevant reference control distribution. Z score values were included for the different disease categories. Z score above 2 or below −2, and in one embodiment, above 3 or below −3, suggests a significant likelihood that the candidate biomarker specifically distinguishes cases from controls [Skates et al. (2007) Cancer EpidemioL Biomarkers Prev. 16(2):334-341]; wherein Z score is [log(value in pool−mean(log(values in appropriate controls))]/SD(log(values in appropriate controls).

(b) Plots illustrating replicate variability—box plots from 20 control pool replicate measures next to the control distribution histogram for some reference of scale.

(c) Tables of control measure distributions across various demographic and clinical characteristics.

The results obtained from analysis of the classical ovarian cancer serum biomarker, CA125 are shown in FIG. 3. The CA125 assay produced the expected profile, with CA125 being a strong biomarker for pelvic diseases. The observation by Skates et al. of a single premenopausal control sample with markedly high CA125 levels was reproduced in this assay setting.

The results obtained from analysis of ovarian cancer serum biomarker, IL-6 are shown in FIG. 4. IL-6 has been suggested as a prognostic indicator for ovarian cancer, though it is not believed to be as sensitive as CA125 (Chan et al. NACB 2006 Draft Guidelines Practice Guidelines for Use of Tumor Markers in the Clinic: Ovarian Cancer) Specific detection of non-mucinous ovarian cancer at early and late stages was observed with the IL-6 assay format described herein. Results for VEGFR-1 (Flt-1) are shown in FIG. 5. The VEGFR-1/Flt-1 assay exhibited better performance in detecting mucinous ovarian cancer than did CA125 and shows it is a significant cancer biomarker, especially for invasive breast cancer in premenopausal women.

The results obtained by screening additional markers of interest to ovarian and endometrial cancers are summarized in FIG. 6. The performances of other markers demonstrating specific detection of pelvic conditions are summarized below in terms of Z scores, comparing to values for CA125 and IL-6. The additional markers of interest include several cytokines/chemokines (IL-1β, IL-2, IL-8, eotaxin 3), a cytokine receptor (TNFR1), inflammation markers (CRP, SM, IL-1β, IL-8), a matrix metalloproteinase (MMP-10), an angiogenesis regulatory factor (Fit-1), and a cell adhesion molecule (P-Cadherin).

In addition, the PLGF assay was able to specifically differentiate invasive breast cancer in premenopausal women from all other conditions and controls and shows it is a useful breast cancer biomarker. The results are shown in FIG. 7.

\*\*\*

Various publications and test methods are cited herein, the disclosures of which are incorporated herein by reference in their entireties. In cases where the present specification and a document incorporated by reference and/or referred to herein include conflicting disclosure, and/or inconsistent use of terminology, and/or the incorporated/referenced documents use or define terms differently than they are used or defined in the present specification, the present specification shall control.

The invention claimed is:

1. A method for diagnosing ovarian cancer in a patient comprising:
   (a) measuring a level of a first biomarker in a serum, plasma, or a combination of serum and plasma sample obtained from a patient, wherein said first biomarker is Flt-1;
   (b) comparing said level of said first biomarker in said sample to a level of said first biomarker in a normal control sample, wherein a level of said first biomarker in said sample that is more than one standard deviation above said level of said first biomarker in said normal control is indicative of the presence of ovarian cancer in said patient; and
   (c) diagnosing from said measuring step and said comparing step the presence or absence of ovarian cancer in said patient.

2. The method of claim 1 wherein said method further comprises measuring a level of at least one additional biomarker in said sample, comparing said level of said at least one additional biomarker in said sample to a level of said at least one additional biomarker in a normal control sample, wherein a level of said at least one additional biomarker in said sample that is more than one standard deviation above said level of said at least one additional biomarker in said normal control is indicative of the presence of ovarian cancer in said patient, and determining from said level of said first biomarker and said level of said at least one additional biomarker the presence or absence of ovarian cancer in said patient.

3. The method of claim 2 wherein said at least one additional biomarker is selected from the group consisting of CA125, IL-6, CRP, SM, IL-8, IL-1β, IL-2, P-Cadherin, Eotaxin-3, TNFR1, OPN, Prolactin, MMP-10, PIGF, and combinations thereof.

4. The method of claim 1 wherein said patient is a premenopausal woman or a postmenopausal woman.

5. The method of claim 1, wherein said measuring step is conducted on a single sample.

6. The method of claim 1, wherein said measuring step is conducted in a single assay chamber.

7. The method of claim 6, wherein said assay chamber is a single well of an assay plate.

8. The method of claim 6, wherein said assay chamber is an assay chamber of a cartridge.

9. The method of claim 1, wherein said sample is selected from the group consisting of blood, serum and plasma.

10. The method of claim 1, wherein said level is measured using an immunoassay.

11. The method of claim 1 wherein the sample is serum.

12. The method of claim 1 wherein said ovarian cancer is non-mucinous ovarian cancer.

13. The method of claim 12 wherein said patient is premenopausal.

14. The method of claim 12 wherein said patient is postmenopausal.

15. The method of claim 1 wherein said ovarian cancer is mucinous ovarian cancer.

16. The method of claim 15 wherein said patient is premenopausal.

17. The method of claim 15 wherein said patient is postmenopausal.

18. The method of claim 1 wherein a level of said first biomarker in said sample that is more than 1.5 standard deviations above said level of said first biomarker in said normal control is indicative of the presence of ovarian cancer in said patient.

19. The method of claim 2 wherein a level of said at least one additional biomarker in said sample that is more than 1.5 standard deviations above said level of said at least one additional biomarker in said normal control is indicative of the presence of ovarian cancer in said patient.

20. The method of claim 1 wherein a level of said first biomarker in said sample that is more than 2.0 standard deviations above said level of said first biomarker in said normal control is indicative of the presence of ovarian cancer in said patient.

21. The method of claim 2 wherein a level of said at least one additional biomarker in said sample that is more than 2.0 standard deviations above said level of said at least one additional biomarker in said normal control is indicative of the presence of ovarian cancer in said patient.

22. The method of claim 1 wherein a level of said first biomarker in said sample that is more than 2.5 standard deviations above said level of said first biomarker in said normal control is indicative of the presence of ovarian cancer in said patient.

23. The method of claim 2 wherein a level of said at least one additional biomarker in said sample that is more than 2.5 standard deviations above said level of said at least one additional biomarker in said normal control is indicative of the presence of ovarian cancer in said patient.

24. The method of claim 1 wherein a level of said first biomarker in said sample that is more than 3.0 standard deviations above said level of said first biomarker in said normal control is indicative of the presence of ovarian cancer in said patient.

25. The method of claim 2 wherein a level of said at least one additional biomarker in said sample that is more than 3.0 standard deviations above said level of said at least one additional biomarker in said normal control is indicative of the presence of ovarian cancer in said patient.

26. The method of claim 2 further comprising determining from said level of said at least one additional biomarker the disease progression of ovarian cancer.

* * * * *